US012697253B2

(12) United States Patent
Hickenbotham et al.

(10) Patent No.: US 12,697,253 B2
(45) Date of Patent: Aug. 4, 2026

(54) SYSTEMS AND METHODS FOR MODULATING LASER TREATMENT ON THE EYE

(71) Applicant: ThruFocus Optics, LLC, Timnath, CO (US)

(72) Inventors: Adam Hickenbotham, Orem, UT (US); Gary Foster, Timnath, CO (US)

(73) Assignee: ThruFocus Optics, LLC, Timnath, CO (US)

( * ) Notice: Subject to any disclaimer, the term of this patent is extended or adjusted under 35 U.S.C. 154(b) by 534 days.

(21) Appl. No.: 18/078,746

(22) Filed: Dec. 9, 2022

(65) Prior Publication Data

US 2024/0189148 A1     Jun. 13, 2024

(51) Int. Cl.
*A61F 9/008*          (2006.01)

(52) U.S. Cl.
CPC .... *A61F 9/008* (2013.01); *A61F 2009/00846* (2013.01); *A61F 2009/00868* (2013.01); *A61F 2009/00878* (2013.01)

(58) Field of Classification Search
None
See application file for complete search history.

(56) References Cited

U.S. PATENT DOCUMENTS

| | | | |
|---|---|---|---|
| 3,930,504 A | 1/1976 | de Laforcade | |
| 5,549,596 A | 8/1996 | Latina | |
| 6,258,082 B1 | 7/2001 | Lin | |

| | | | |
|---|---|---|---|
| 6,263,879 B1 | 7/2001 | Lin | |
| 6,325,792 B1 | 12/2001 | Swinger et al. | |
| 6,357,875 B1 | 3/2002 | Herrick | |
| 6,814,729 B2 | 11/2004 | Youssefi et al. | |
| 8,202,268 B1 | 6/2012 | Wells et al. | |
| 9,232,959 B2 | 1/2016 | Aljuri et al. | |
| 9,345,549 B2 | 5/2016 | Hickenbotham | |
| 9,427,358 B2 | 8/2016 | Mordaunt et al. | |
| 9,949,749 B2 | 4/2018 | Noonan et al. | |
| 10,231,867 B2 | 3/2019 | Alvarez et al. | |
| 10,285,574 B2 | 5/2019 | Landey et al. | |
| 10,398,599 B2 | 9/2019 | Charles | |
| 10,406,352 B2 | 9/2019 | Kurtz et al. | |
| 10,406,380 B2 | 9/2019 | Kurtz et al. | |

(Continued)

FOREIGN PATENT DOCUMENTS

| | | |
|---|---|---|
| CA | 2874220 C | 5/2021 |
| CN | 104968308 A | 10/2015 |

(Continued)

OTHER PUBLICATIONS

Bhattacharyya, B.,"Step by Step, Laser in Opthamology," Jaypee Brothers Medical Publishers , 2009, 247 pages.

(Continued)

*Primary Examiner* — Lynsey C Eiseman
(74) *Attorney, Agent, or Firm* — Zilka-Kotab, P.C.

(57)          ABSTRACT

Systems and methods are provided for modulating laser treatment on the eye. In use, an eye of a patient is scanned using a laser scanning system to produce a scan result. A mapping of the eye is created based on the scan result. Additionally, a modulated treatment of the eye is created based on the mapping. Further, a laser illumination light beam is delivered to a first location on the eye of the patient in accordance with the modulated treatment.

20 Claims, 20 Drawing Sheets

100

(56) References Cited

U.S. PATENT DOCUMENTS

| | | | |
|---|---|---|---|
| 10,548,771 | B2 | 2/2020 | Coleman et al. |
| 10,744,035 | B2 | 8/2020 | Alvarez et al. |
| 10,758,413 | B2 | 9/2020 | Telandro |
| 10,959,792 | B1 | 3/2021 | Huang et al. |
| 11,357,586 | B2 | 6/2022 | Huang et al. |
| 2002/0049450 | A1 | 4/2002 | Myers |
| 2002/0101564 | A1 | 8/2002 | Herrick |
| 2002/0161365 | A1 | 10/2002 | Martins |
| 2002/0167644 | A1 | 11/2002 | Pollack et al. |
| 2004/0030269 | A1 | 2/2004 | Horn et al. |
| 2005/0049584 | A1 | 3/2005 | Homer |
| 2005/0165385 | A1 | 7/2005 | Simon |
| 2005/0205101 | A1 | 9/2005 | Lin |
| 2007/0055220 | A1 | 3/2007 | Lin et al. |
| 2008/0015553 | A1 | 1/2008 | Zacharias |
| 2008/0243108 | A1 | 10/2008 | Murakami et al. |
| 2009/0051872 | A1 | 2/2009 | Volk |
| 2010/0016395 | A1 | 1/2010 | Benozzi |
| 2011/0001926 | A1* | 1/2011 | Mann .................. A61F 9/00821 |
| | | | 385/33 |
| 2011/0160622 | A1 | 6/2011 | McArdle et al. |
| 2013/0226161 | A1 | 8/2013 | Hickenbotham |
| 2013/0289450 | A1 | 10/2013 | Homer |
| 2014/0128854 | A1 | 5/2014 | McArdle et al. |
| 2014/0148737 | A1 | 5/2014 | Homer |
| 2014/0228825 | A1 | 8/2014 | Gorschboth et al. |
| 2014/0316390 | A1 | 10/2014 | Chernyak |
| 2016/0089269 | A1 | 3/2016 | Horvath et al. |
| 2016/0365697 | A1 | 12/2016 | Hori et al. |
| 2017/0027756 | A1 | 2/2017 | Angeley et al. |
| 2017/0143543 | A1 | 5/2017 | McArdle |
| 2017/0238798 | A1* | 8/2017 | Isogai .................. A61B 3/1005 |
| 2017/0266041 | A1* | 9/2017 | Kim ......................... A61B 3/12 |
| 2018/0085257 | A1* | 3/2018 | Horvath .............. A61F 9/00834 |
| 2018/0103837 | A1 | 4/2018 | Kurtz et al. |
| 2018/0104098 | A1 | 4/2018 | Kurtz et al. |
| 2018/0104099 | A1 | 4/2018 | Kurtz et al. |
| 2018/0104508 | A1 | 4/2018 | Kurtz et al. |
| 2018/0214305 | A1 | 8/2018 | Schuele et al. |
| 2020/0038239 | A1 | 2/2020 | Mikula et al. |
| 2020/0146887 | A1 | 5/2020 | Horvath et al. |
| 2022/0031508 | A1 | 2/2022 | Dennison et al. |
| 2022/0304850 | A1* | 9/2022 | Homer .................... A61F 9/008 |
| 2023/0372153 | A1* | 11/2023 | Katchinskiy ........... A61B 34/25 |

FOREIGN PATENT DOCUMENTS

| | | | |
|---|---|---|---|
| CN | 112367928 | A | 2/2021 |
| CN | 112566567 | A | 3/2021 |
| EP | 2259742 | A4 | 12/2011 |
| EP | 2816965 | A2 | 12/2014 |
| EP | 3062750 | B1 | 4/2021 |
| EP | 3813714 | A4 | 2/2022 |
| ES | 2253141 | T3 | 4/2015 |
| ES | 2687817 | T3 | 10/2018 |
| ES | 2833281 | T3 | 6/2021 |
| JP | 2007133333 | A | 5/2007 |
| JP | 6114761 | B2 | 4/2017 |
| JP | 2017104597 | A | 6/2017 |
| KR | 20140144687 | A | 12/2014 |
| WO | 201312683 | A2 | 1/2013 |
| WO | 2015068205 | A1 | 5/2015 |
| WO | 2018071733 | A1 | 4/2018 |
| WO | 2018187069 | A1 | 10/2018 |
| WO | 2020036685 | A1 | 2/2020 |
| WO | 2020263629 | A1 | 12/2020 |
| WO | 2020263949 | A1 | 12/2020 |
| WO | 2021137071 | A1 | 7/2021 |

OTHER PUBLICATIONS

Juthani et al., "Corneal Crosslinking in Refractive Corrections," Translational Vision Science & Technology, vol. 10, No. 5, Apr. 2021, pp. 1-9.

Waring et al., "Cornea-Based Techniques and Technology for Surgical Correction of Presbyopia," Current Ophthalmology Reports, vol. 2, 2014,pp. 41-47.

Hickenbotham, A., U.S. Appl. No. 61/603,281, filed Feb. 25, 2012.

Hickenbotham et al., U.S. Appl. No. 13/775,071, filed Feb. 22, 2013.

Hickenbotham, A., PCT Application No. PCT/US2013/027509, filed Feb. 22, 2013.

International Search Report from PCT Application No. PCT/US2013/027509, dated May 13, 2013.

Schwarzenbacher et al., "Prostaglandin Release After Low-Energy Femtosecond Laser-Assisted Cataract Surgery Without Anti-Inflammatory Drug Premedication," American Journal of Ophthalmology, vol. 238, Jun. 2022, pp. 103-109.

Yu et al., "Tissue effects of intra-tissue refractive index shaping (IRIS): insights from two-photon autofluorescence and second harmonic generation microscopy," Biomedical Optics Express, vol. 10, No. 2, Feb. 1, 2019, pp. 855-867.

Mohammad, S., "Lasers Uses in Opthamology," Journal of Postgraduate Medical Institute (JPMI), vol. 11, No. 2, pp. 111-123.

Supplementary European Search Report for EP Application No. 13751556, for Thrufocus Optics, Inc., dated Jan. 11, 2016.

Hill et al., "Ab-Interno Erbium (Er):YAG Laser Sclerostomy With Iridotomy in Dutch Cross Rabbits," Lasers in Surgery and Medicine, vol. 13, 1993, pp. 559-564.

Turkcu et al., "Corneal perforation during Nd:YAG laser capsulotomy: a case report," International Ophthalmology, vol. 33, 2013, pp. 99-101.

Raju et al., "Technological advances in intraocular lens surgery," Clinical Refractive Surgery, Optician, Aug. 2016, pp. 32-34.

Kugler et al., "Lasers in refractive surgery: history, present, and future," Applied Optics, vol. 49, No. 25, Sep. 1, 2010, pp. F1-F9.

Stopa et al., "Sutureless Iris Repair: Cauterization Technique," Retina, The Journal of Retinal and Vitreous Diseases, vol. 35, No. 12, pp. 2647-2649.

Sugar, A., "Ultrafast (femtosecond) laser refractive surgery," Current Opinion in Ophthalmology, vol. 13, 2002, pp. 246-249.

Savage, D., "A Non-Ablative Technique for Femtosecond Laser-Based Refractive Correction: Development, Efficacy, and Tissue Effects," Dissertation, The Institute of Optics Arts, Sciences, and Engineering, Edmund A. Hajim School of Engineering and Applied Sciences, 2018, 366 pages.

* cited by examiner

100

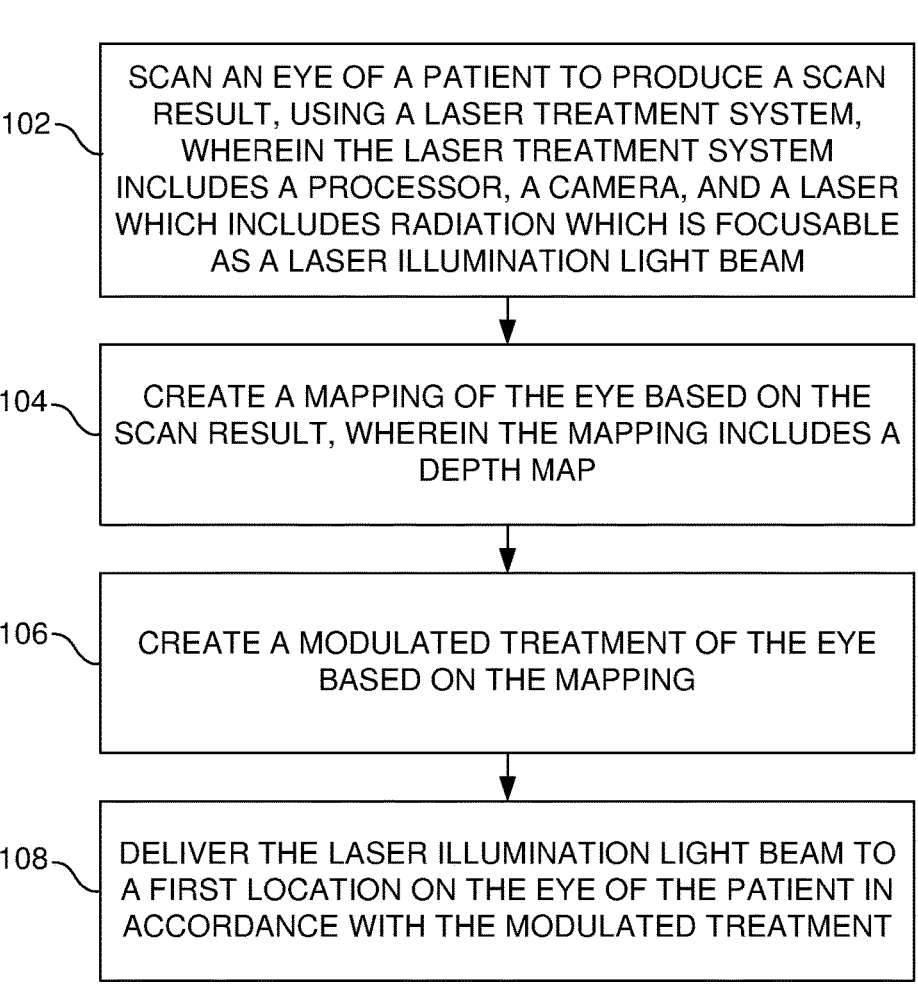

102 — SCAN AN EYE OF A PATIENT TO PRODUCE A SCAN RESULT, USING A LASER TREATMENT SYSTEM, WHEREIN THE LASER TREATMENT SYSTEM INCLUDES A PROCESSOR, A CAMERA, AND A LASER WHICH INCLUDES RADIATION WHICH IS FOCUSABLE AS A LASER ILLUMINATION LIGHT BEAM

104 — CREATE A MAPPING OF THE EYE BASED ON THE SCAN RESULT, WHEREIN THE MAPPING INCLUDES A DEPTH MAP

106 — CREATE A MODULATED TREATMENT OF THE EYE BASED ON THE MAPPING

108 — DELIVER THE LASER ILLUMINATION LIGHT BEAM TO A FIRST LOCATION ON THE EYE OF THE PATIENT IN ACCORDANCE WITH THE MODULATED TREATMENT

205
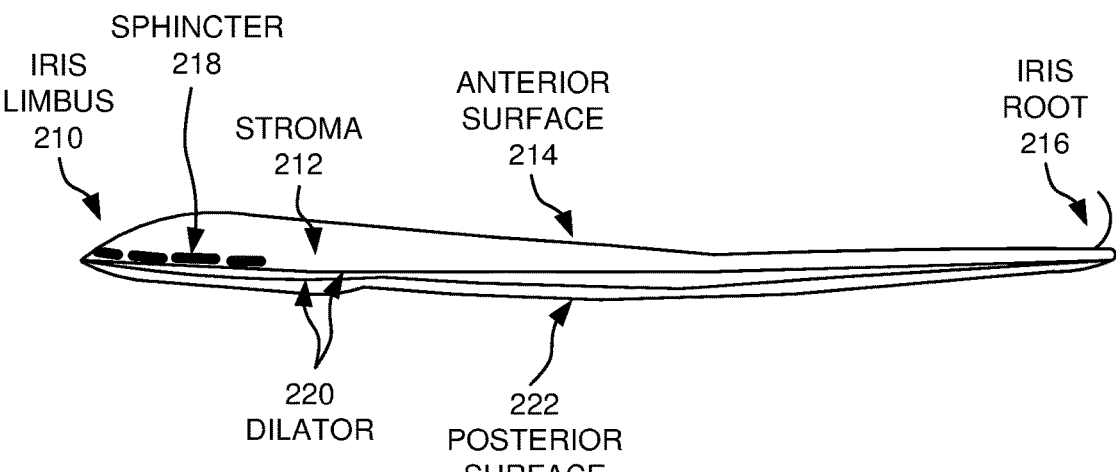
IRIS
LIMBUS
210
SPHINCTER
218
STROMA
212
ANTERIOR
SURFACE
214
IRIS
ROOT
216
220
DILATOR
222
POSTERIOR
SURFACE
FIG. 2C 500
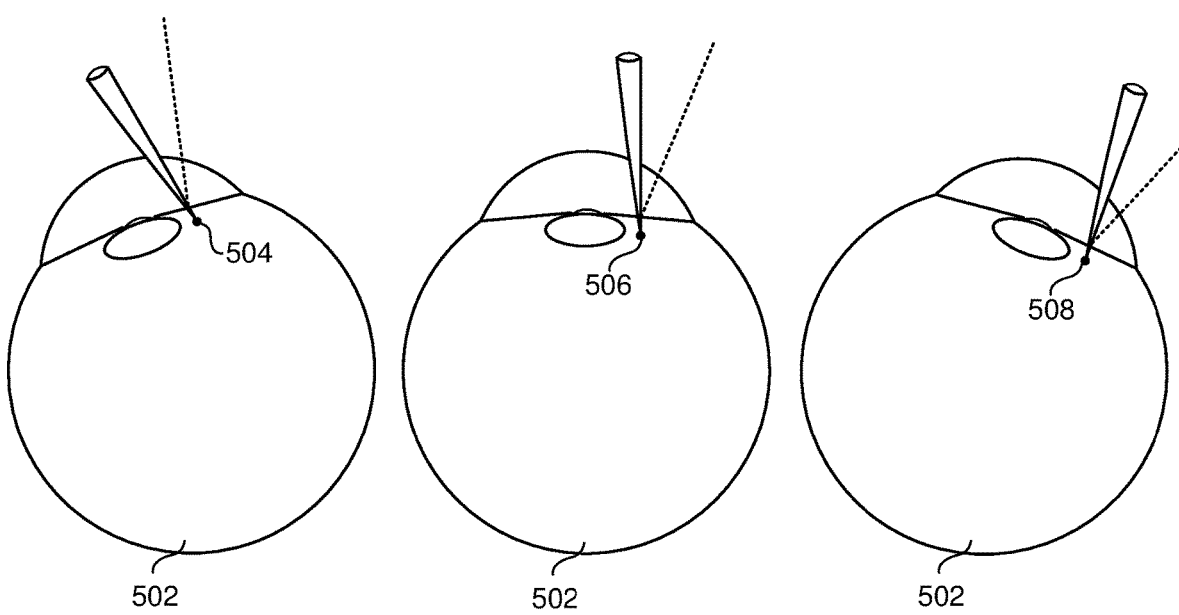
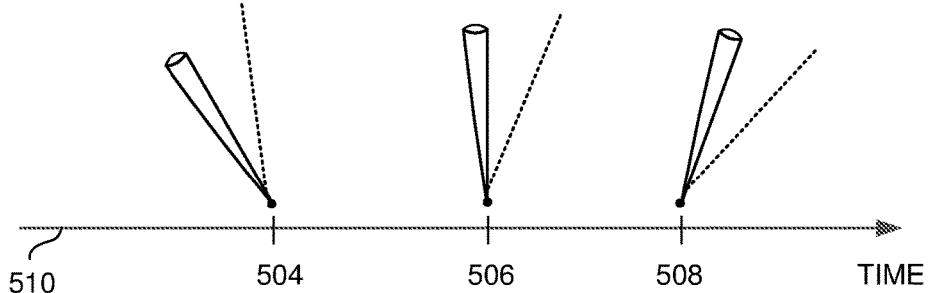
FIG. 5

600

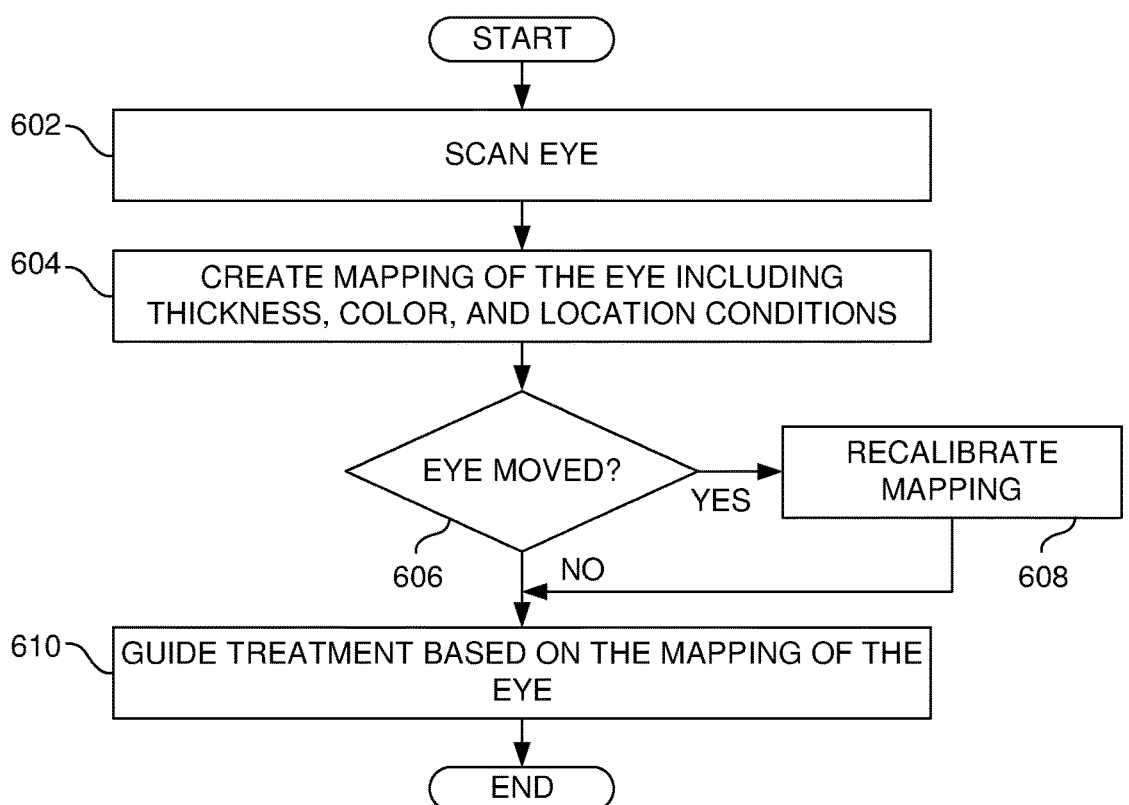

```
                    ┌──────────┐
                    │  START   │
                    └──────────┘
                          │
                          ▼
602 ──┌──────────────────────────────────────────────┐
      │                  SCAN EYE                      │
      └──────────────────────────────────────────────┘
                          │
                          ▼
604 ──┌──────────────────────────────────────────────┐
      │  CREATE MAPPING OF THE EYE INCLUDING           │
      │  THICKNESS, COLOR, AND LOCATION CONDITIONS     │
      └──────────────────────────────────────────────┘
                          │
                          ▼
                    ╱─────────────╲            ┌──────────────────┐
                   ╱  EYE MOVED?    ╲   YES     │   RECALIBRATE    │
                   ╲                ╱──────────▶│    MAPPING       │
                    ╲─────────────╱             └──────────────────┘
                    606      │  NO                      608
                             ▼
610 ──┌──────────────────────────────────────────────┐
      │  GUIDE TREATMENT BASED ON THE MAPPING OF THE   │
      │                   EYE                           │
      └──────────────────────────────────────────────┘
                          │
                          ▼
                    ┌──────────┐
                    │   END    │
                    └──────────┘
```

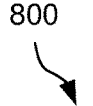

800

802                804

| EYE COLOR | LASER PREDEFINED INSTRUCTIONS |
|---|---|
| RED | EFFECTIVE PULSE 1 / EFFECTIVE DEPTH 1 |
| LIGHT BLUE | EFFECTIVE PULSE 2 / EFFECTIVE DEPTH 2 |
| BLUE | EFFECTIVE PULSE 3 / EFFECTIVE DEPTH 3 |
| BLUE-GRAY | EFFECTIVE PULSE 4 / EFFECTIVE DEPTH 4 |
| GRAY | EFFECTIVE PULSE 5 / EFFECTIVE DEPTH 5 |
| GRAY-GREEN | EFFECTIVE PULSE 6 / EFFECTIVE DEPTH 6 |
| GREEN | EFFECTIVE PULSE 7 / EFFECTIVE DEPTH 7 |
| HAZEL | EFFECTIVE PULSE 8 / EFFECTIVE DEPTH 8 |
| AMBER | EFFECTIVE PULSE 9 / EFFECTIVE DEPTH 9 |
| LIGHT BROWN | EFFECTIVE PULSE 10 / EFFECTIVE DEPTH 10 |
| MEDIUM BROWN | EFFECTIVE PULSE 11 / EFFECTIVE DEPTH 11 |
| DARK BROWN | EFFECTIVE PULSE 12 / EFFECTIVE DEPTH 12 |
| BLACK | EFFECTIVE PULSE 13 / EFFECTIVE DEPTH 13 |

806

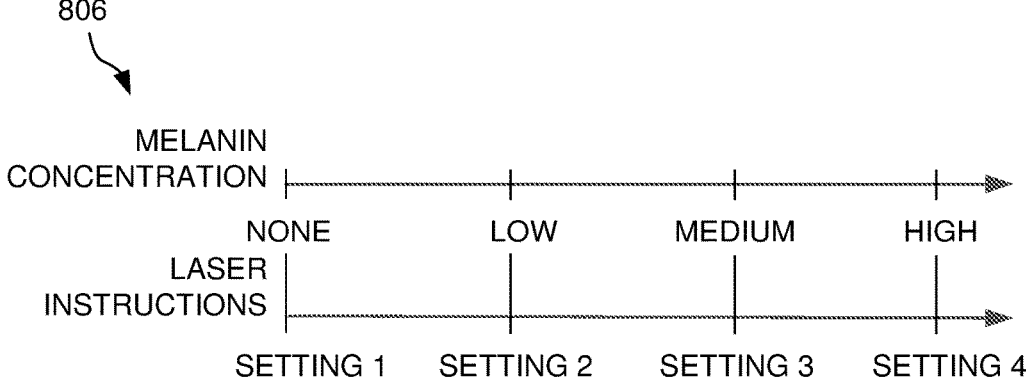

START

902 — DETERMINE COLOR OF EYE BASED ON THE MAPPING OF THE EYE

904 — CREATE COLOR MAP OF THE EYE

906 — CREATE CALIBRATED POWER MAP BASED ON THE COLOR MAP

908 — GUIDE TREATMENT BASED ON THE MAPPING OF THE EYE AND THE CALIBRATED POWER MAP

END

1100

1800
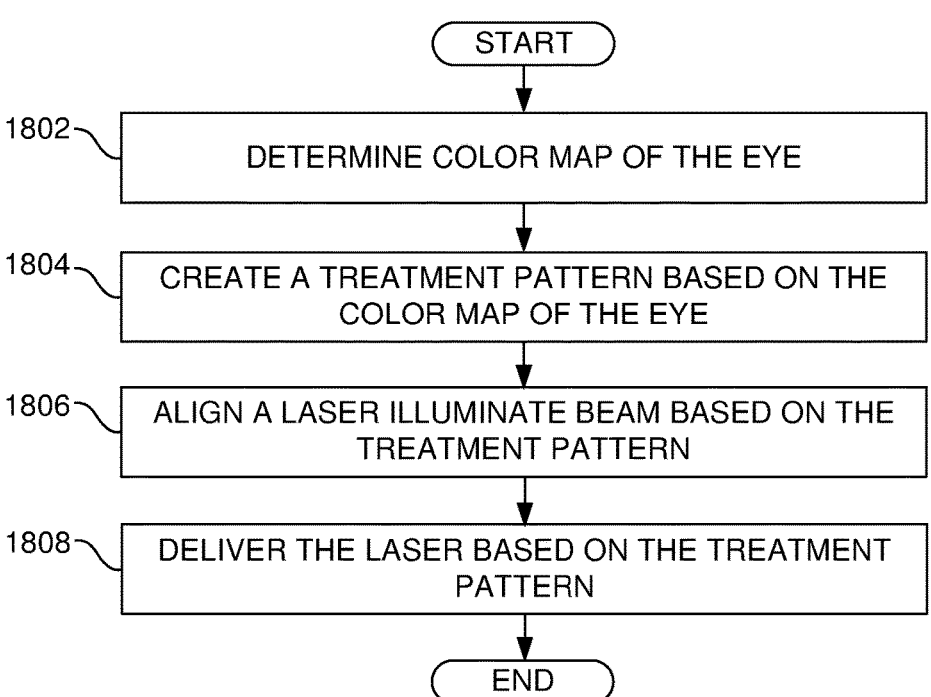
START
1802 — DETERMINE COLOR MAP OF THE EYE
1804 — CREATE A TREATMENT PATTERN BASED ON THE COLOR MAP OF THE EYE
1806 — ALIGN A LASER ILLUMINATE BEAM BASED ON THE TREATMENT PATTERN
1808 — DELIVER THE LASER BASED ON THE TREATMENT PATTERN
END
FIG. 18

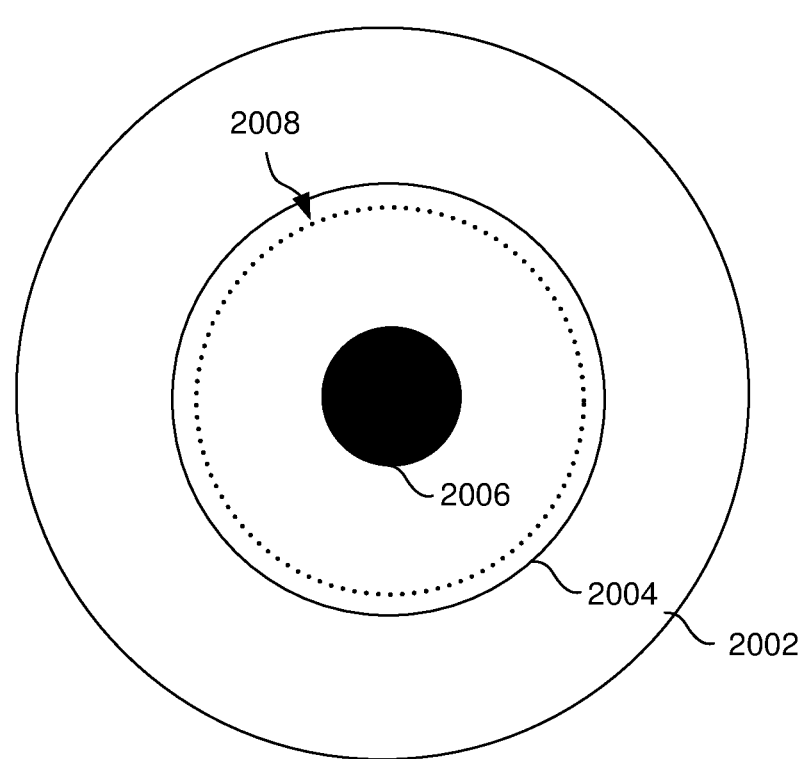
FIG. 20

SYSTEMS AND METHODS FOR MODULATING LASER TREATMENT ON THE EYE

RELATED APPLICATIONS

The application relates to and incorporates by reference for all purposes the following applications: U.S. patent application Ser. No. 13/775,071 (issued as U.S. Pat. No. 9,345,549), filed 2013 Feb. 22 and entitled "DEVICES AND METHODS FOR IMPROVING VISION USING LASER PHOTOMIOSIS;" and U.S. Provisional Patent Application No. 61/603,281, filed 2012 Feb. 25 and entitled "METHOD FOR LASER REDUCTIVE COREOPLASTY."

FIELD OF THE INVENTION

The present invention relates to treating eye disorders, and more particularly to modulating laser treatment on the eye.

BACKGROUND

Currently, treatment methods for treating eye disorders (including, for example, presbyopia) are limited in effectiveness and require oftentimes invasive surgical procedures or ongoing eye drops. For example, pharmacological treatment may be used to constrict pupils (by stimulating specific eye muscles to contract). However, it is generally used on a short-term basis due to decreasing efficacy and potential adverse side effects. Alternatively, corrective surgical procedures may be used to alter the focal distance of the human eye lens in order to correct nearsightedness which reduces the distance vision of the treated eye. However, such surgical procedures may not fully correct the effects of the eye disorder (such as presbyopia).

As such, there is thus a need for addressing these and/or other issues associated with the prior art.

SUMMARY

Systems and methods are provided for modulating laser treatment on the eye. In use, an eye of a patient is scanned using a laser scanning system to produce a scan result. A mapping of the eye is created based on the scan result. Additionally, a modulated treatment of the eye is created based on the mapping. Further, a laser illumination light beam is delivered to a first location on the eye of the patient in accordance with the modulated treatment.

BRIEF DESCRIPTION OF THE DRAWINGS

FIG. 1 illustrates a method for modulating laser treatment on the eye, in accordance with one embodiment.

FIG. 2C illustrates a close up view of the iris, in accordance with one embodiment.

FIG. 5 illustrates a laser offset treatment at multiple eye positions, in accordance with one embodiment.

FIG. 6 illustrates a method for guiding treatment based on a mapping of the eye, in accordance with one embodiment.

FIG. 8 illustrates a table of eye color correlations, in accordance with one embodiment.

FIG. 18 illustrates a method for creating a treatment pattern based on a color map of the eye, in accordance with one embodiment.

FIG. 20 illustrates an exemplary pattern, in accordance with one embodiment.

DETAILED DESCRIPTION

Figure 2A:
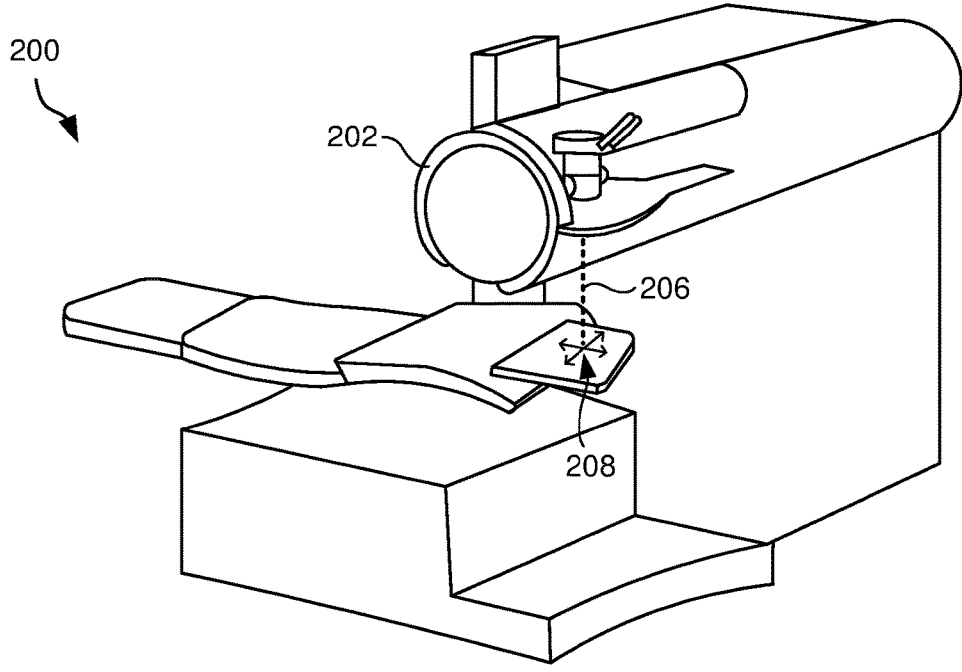
FIG. 2A illustrates an exemplary modulating laser treatment system, in accordance with one embodiment.

A key treatment of age-related issues in the fields of optometry and ophthalmology is assisting patients who experience the onset of presbyopia, which compromises the natural optical lens in the human eye that traditionally handles the human body's ability to alter focal length which provides for superior focus and ability to see very small objects up close.

As presented herein, new methods and techniques are provided for laser treatment of the eyes. Such techniques include visible tissue response that may guide subsequent laser treating of the eye, providing a spot-delivery laser treatment that is based on a pre-measurement of the ideal depth of the laser treatment, providing ideal laser power parameters based on premeasured or in situ measured optical density, providing an ability to cross-link corneas from within the eye (not merely on the surface), providing the ability to crosslink the iris tissues, using a color identification of the iris to correlate an appropriate power of the laser for the laser treatment, using eye-specific patterns based on a pre-scan of the eye or in situ scan, using a spot by spot scan to determine the efficacy of a placed laser spot to determine the power of the subsequent or subsequent spots, providing the ability for thermal measurement of laser post uptake of iris pulses to determine spot efficacy and or to dictate the power settings for subsequent spots, and/or integrating a variety of laser pulses independent of or in combination with the foregoing.

Definitions and Use of Figures

Some of the terms used in this description are defined below for easy reference. The presented terms and their respective definitions are not rigidly restricted to these definitions-a term may be further defined by the term's use within this disclosure. The term "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application and the appended claims, the term "or" is intended to mean an inclusive "or" rather than an exclusive "or". That is, unless specified otherwise, or is clear from the context, "X employs A or B" is intended to mean any of the natural inclusive permutations. That is, if X employs A, X employs B, or X employs both A and B, then "X employs A or B" is satisfied under any of the foregoing instances. As used herein, at least one of A or B means at least one of A, or at least one of B, or at least one of both A and B. In other words, this phrase is disjunctive. The articles "a" and "an" as used in this application and the appended claims should generally be construed to mean "one or more" unless specified otherwise or is clear from the context to be directed to a singular form.

Various embodiments are described herein with reference to the figures. It should be noted that the figures are not necessarily drawn to scale, and that elements of similar structures or functions are sometimes represented by like reference characters throughout the figures. It should also be noted that the figures are only intended to facilitate the description of the disclosed embodiments-they are not representative of an exhaustive treatment of all possible embodiments, and they are not intended to impute any limitation as to the scope of the claims. In addition, an illustrated embodiment need not portray all aspects or advantages of usage in any particular environment.

An aspect or an advantage described in conjunction with a particular embodiment is not necessarily limited to that embodiment and can be practiced in any other embodiments even if not so illustrated. References throughout this specification to "some embodiments" or "other embodiments" refer to a particular feature, structure, material or characteristic described in connection with the embodiments as being included in at least one embodiment. Thus, the appearance of the phrases "in some embodiments" or "in other embodiments" in various places throughout this specification are not necessarily referring to the same embodiment or embodiments. The disclosed embodiments are not intended to be limiting of the claims.

Within the context of the present description, laser treatment includes any laser therapy that uses focused light for treatment. Additionally, the term modulate may refer to the ability to control or modify the laser treatment. The term mapping may refer to a topography map of the surface of the eye, a thickness map of the eye, a combination of the foregoing, and/or any map associated with the eye. The term burning, as used within the context of the present description, may encompass any or all of altering the tissue, heating, cutting, weakening, and/or creating a scar. As such, the term burning may include alteration.

Descriptions of Exemplary Embodiments

FIG. 1 illustrates a method 100 for modulating laser treatment on the eye, in accordance with one embodiment.

As shown, the method 100 comprises scanning an eye of a patient to produce a scan result, using a laser treatment system, wherein the laser treatment system includes a processor, a sensor (including but not limited to a camera, an infrared sensor, a photoelectric sensor, etc.), a laser where the radiation of which is focusable as a laser illumination light beam. See operation 102. For example, the scan result may occur by a variety of methods including optical coherence tomography (OCT), ultrasound, etc. In some embodiments, the scanning may be a pre-scan that is separated from the subsequent treatment. For example, the scanning may occur hours (or any amount of time prior) before the actual laser treatment. In this manner, the scanning may be reviewed and discussed with the patient prior to implementation. In other embodiments, the scanning may be a pre-scan of the eye immediately prior to the laser treatment being implemented. Further, scanning may include in one embodiment both an advance scanning (hours/days/weeks before the laser treatment) and a pre-scan (immediately before the treatment) to ensure that the initial advance scanning results are consistent with the pre-scan results (i.e. no change has occurred).

Figure 3:
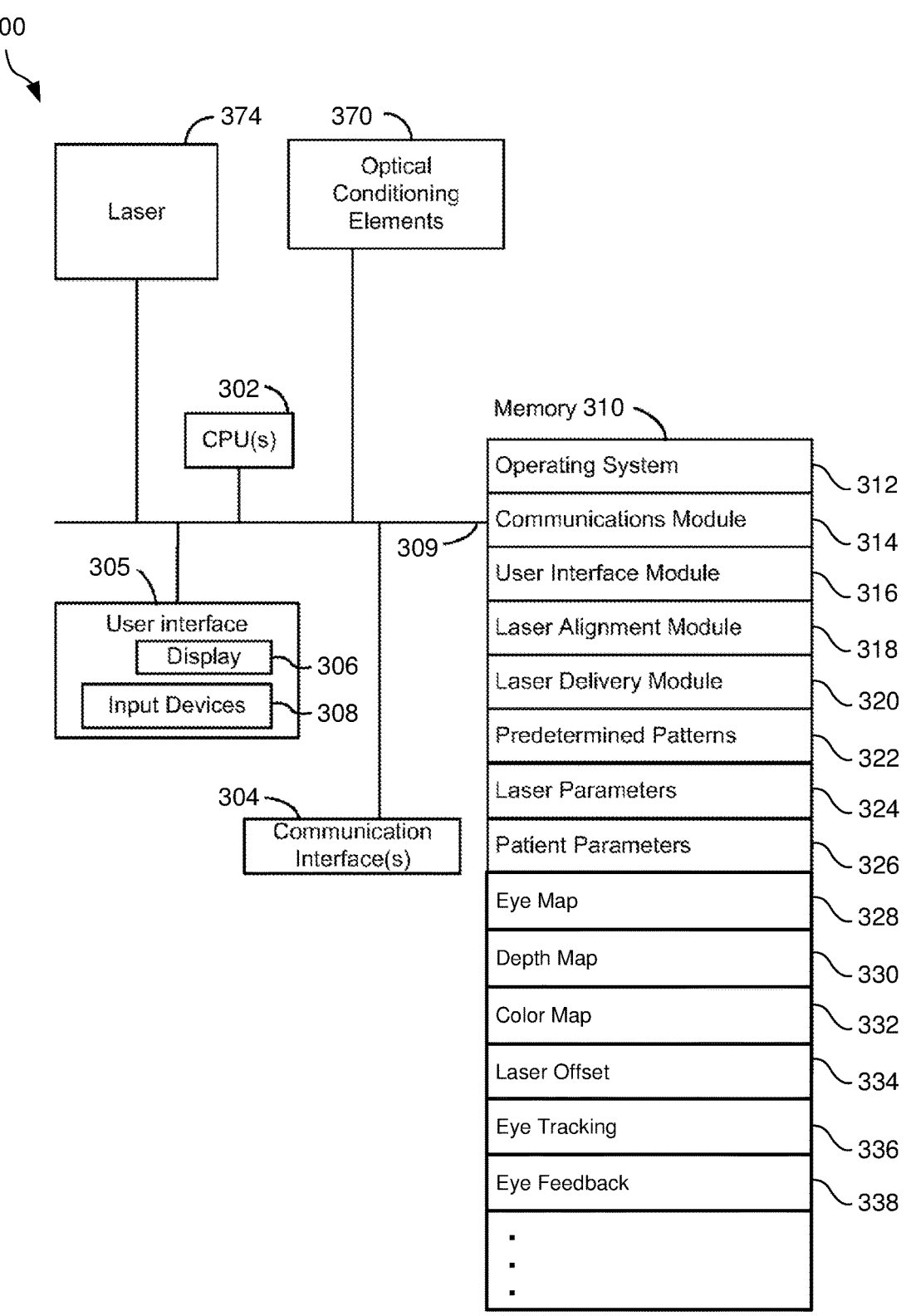
FIG. 3 illustrates a block diagram illustrating the modulating laser treatment system, in accordance with one embodiment.

Additionally, the method 100 comprises creating a mapping of the eye based on the scan result, wherein the mapping includes a depth map, optical density map, and/or color map (see herein FIG. 3 depth map 330 as an example of one type of a map). See operation 104. The scan result may be used to determine the depth map, optical density map, and/or or color map of the eye. It should be noted that when reference is made herein to the "eye", such reference includes any and all parts of the eye which may be subject to examination and treatment (including, for example, the iris). Additionally, the scan result may include determining a thickness of the iris (or any intended area of the eye). In this manner, a mapping of the thickness throughout the entire eye may be obtained.

Further, the method 100 comprises creating a modulated treatment of the eye based on the mapping. See operation 106. In one embodiment, the modulated treatment may be implemented in an environment where the laser is a pulse laser and the laser illumination light beam comprises a sequence of multiple light pulses, where the average repetition rate between two consecutive light pulses is between 0.5 Hertz and 100 kiloHertz. In another embodiment, the modulated treatment may include various sequences of light pulse durations between 10 milliseconds and 100 milliseconds, 1 millisecond and 10 milliseconds, and 100 femtoseconds and 1 millisecond. Of course, it is to be appreciated that the light pulse durations may be configured in any manner to provide a modulated laser treatment to the patient.

The modulated treatment may include composing an eye-specific pattern based on the mapping (such as the depth map, topical density, and/or color map). For example, the contours of the eye may have, in one location, a smaller thickness, and at a second location, a larger thickness. Additionally, the modulated treatment may include composing an eye-specific pattern based on the surface topology of the eye and/or the shape of the eye (or any other part of the eye, such as the iris, which may be the subject of treatment). For example, an iris may not be perfectly round, or the eye surface may not be perfectly curved. The pattern therefore may be specific to the surface contours and shape of the eye. The modulated treatment may take into consideration such variances such that the laser treatment delivered to the eye remains consistent at all locations notwithstanding variances in thickness, contours, and/or shape. In this manner, the modulated treatment may be patient eye-specific and include patient eye-specific patterns, preconfigured laser treatment power, preconfigured laser pulse durations, etc.

Still yet, the modulated treatment may include a predetermined pattern, a predetermined depth, predetermined power settings, and/or any combination of the foregoing. Additionally, the color may refer to a color of the eye, and such eye color may be associated with an effective pulse of the laser illumination light beam and an effective depth of the laser illumination light beam. The eye color, therefore, may be associated with the current color of the eye (to direct and guide the laser treatment) and/or may be associated with a to-be-desired color of the eye. For example, if it were desired to change one's eye color from brown to blue, the modulated treatment may include determining the current color of the eye (brown) and creating a treatment to change the current color to blue (or any desired color). For example, brown melanin that is present in the anterior layers of the iris may be removed via the laser treatment (thereby rendering the eye a blue color), consistent with the modulated treatment.

In addition, the method 100 comprises delivering the laser illumination light beam to a first location on the eye of the patient in accordance with the modulated treatment. See operation 108. Delivering the laser illumination light beam may include treating the eye consistent with the modulated treatment that was created (see operation 106). In one embodiment, delivering the laser illumination light beam may include using the laser illumination light beam to burn a subset of the eye's iris dilator muscle tissue, thus decreasing the diameter of the patient's pupil. For example, burning the eye muscle tissue may reduce the muscle tissue to dilate the pupil of the eye. Such reduction in dilating of the pupil may cause, in turn, a reduction of defocus blur and visual aberrations.

In another embodiment, delivering the laser illumination light beam may involve tracking the eye while delivering the laser illumination light beam to the first location on the eye or to the one or more second locations on the eye, and then optionally, guiding the laser illumination light beam based on that tracking. The scan result (per operation 104) detailed herein may be used to not only determine eye characteristics (such as topology, thickness, contours, shape, etc.), may be also used to determine location points of the eye (such as a 2d or 3d mesh representation of the eye). In this manner, should the eye move during the course of treatment, the eye location points may be accordingly moved (in a synced fashion) such that the modulated treatment remains current and correct regardless of the movement of the eye. Such synced updating between the movement of the eye and the eye location points may occur once every 100-1000th of a second (i.e. every millisecond), and/or any predetermined time interval. Still yet, the tracking may occur may via video frames or individual photo frames. Such tracking may also be used to ensure that predetermined patterns are delivered at the intended locations, and that the predetermined locations of certain anatomical spots (such as blood vessels) are avoided. If in situ scans (such as but not limited to color, depth, optical density, or thermal uptake) are utilized, tracking may help place the subsequent spots delivered at their best location as related to the previously delivered spots. Additionally, delivering the laser illumination light beam may include a contact probe (e.g. placed on the cornea) that delivers a predetermined wavelength of light. In this manner, the beam of light of the laser illumination light beam may be transmitted through the sclera (to the iris root).

Further still, in one embodiment the method 100 may comprise receiving feedback for the modulated treatment based on the delivering of the laser illumination light beam to the first location on the eye, using the laser treatment system. Additionally, when the feedback aligns with expected results of the modulated treatment, the laser illumination light beam may be delivered to one or more second locations on the eye of the patient in accordance with the modulated treatment. Further, when the feedback conflicts with the expected results of the modulated treatment, the modulated treatment may be updated based on the feedback, and the laser illumination light beam may be delivered to the one or more second locations on the eye of the patient in accordance with the updated modulated treatment. In this manner, the modulated treatment may include not only a preconfigured pre-treatment laser plan, but based on results from the treatment, may modify the original modulated treatment to ensure an effective treatment.

In one embodiment, the method 100 may allow for altering the laser delivery process based on feedback provided in the form of the eye's muscle responses. In order to perceive adequate feedback for appropriate adjustment and/or remediation of modulated treatment, the user may need to increase or decrease the power/wattage or length of laser pulse of the laser employed in said treatment so that a visible response may be observed or detected by in situ scan and, subsequently, acted upon to adjust or modulate the treatment. By way of example, per operation 108, the laser illumination beam may be delivered to a first location on the eye, consistent with the modulated treatment. If the eye responds (gives a muscle response), such may be indicative that the laser has sufficiently penetrated the eye such that the location has been burned. Alternatively, if the eye does not respond, such may be indicative that the laser has not sufficiently penetrated the eye. In that manner, the power/wattage, and/or the pulse duration, may be altered and increased. Such adjustment(s) may be made by the surgeon or by algorithm.

In one embodiment, treatment of the patient's iris may involve employing the capabilities of optical coherence tomography (OCT) in order to develop an image of the iris and develop a pattern for treatment based on those measurements. In such an application, it is understood that known wavelengths may be optimally used consistent with known eye conditions. For example, a 1064 wavelength may be used to achieve the objective of mapping and determining depth of the iris tissue in a patient's eye in multiple locations—where it is understood that the iris tissue is thicker in some places and thinner in others; where it is understood that optical density of tissue may vary. As a result, the modulating laser treatment model may include one or more variances in laser power to deliver during treatment based on the mapping developed through the use of OCT.

In a further embodiment, modulated treatment may take place on a spot-by-spot basis. Thus, in one example, an active OCT may be connected to the user's laser delivery slit lamp viewing device during the procedure, where the OCT is then able to determine whether the last treatment spot was of the appropriate depth (not too deep or too shallow) and dense enough in delivery to produce the desired treatment result. Further, ultrasound technology and/or thermal imaging may each be used to determine the effectiveness of treatment (in addition to the fact that OCT and ultrasound may be used to do a scan of the eye as detailed hereinabove).

In this manner, the modulated treatment may function as an iterative improvement process where information gleaned from the last applied spot on the eye may be used to guide the configuration for the subsequent spot.

It is to be appreciated that the methods detailed herein may relate to a variety of other scenarios. For example, such treatment may apply regardless of the position of the patient (seated versus laying down), assuming the head is secured. Additionally, the method 100 may be used in the context of cross-linking corneas (to strengthen the cornea), where treatment may be applied in the anterior layers of the eye (i.e. below the surface). Additionally, the treatment methods could be with direct contact of the cornea or indirectly (such as through air). The treatment could also be direct contact with the iris via an Endo probe or thermal cautery.

More illustrative information will now be set forth regarding various optional architectures and uses in which the foregoing method may or may not be implemented, per the desires of the user. It should be strongly noted that the following information is set forth for illustrative purposes and should not be construed as limiting in any manner. Any of the following features may be optionally incorporated with or without the exclusion of other features described.

FIG. 2A illustrates an exemplary modulating laser treatment system 200, in accordance with one embodiment. As an option, the system 200 may be implemented in the context of any one or more of the embodiments set forth in any previous and/or subsequent figure(s) and/or description thereof. Of course, however, the system 200 may be implemented in the context of any desired environment. Further, the aforementioned definitions may equally apply to the description below.

As shown, the system 200 may be comprised of a laser apparatus 202, a patient treatment bed 204, a laser treatment beam 206, and the ability to modulate the direction of the treatment beam 208. It is to be appreciated that the system 200 represents just one configuration, and that other alterations (i.e. portable, transportable, etc.) are envisioned.

In operation, a patient may lay on the patient treatment bed 204 and the laser apparatus 202 may be used to scan an eye of the patient to produce a scan result (consistent with operation 102), create a mapping of the eye based on the scan result (consistent with operation 104), and create a modulated treatment of the eye based on the mapping (consistent with operation 106). The laser treatment beam 206 may be delivered to the eye of the patient (consistent with operation 108). Additionally, based on feedback received for the modulated treatment, the laser treatment beam may be altered. The ability to modulate the direction of the treatment beam 208 may occur based on the x-axis plane, the y-axis plane, and/or the z-axis plane, and/or any combination of the foregoing. In this manner, for example, should the eye move, the position of the treatment beam may be altered in accordance with the modulated treatment. It is to be appreciated that a housing of the treatment beam 208 may be physically moved (in that the housing unit of the treatment beam may be moved in any direction), and/or the treatment beam itself may be moved in any direction.

In various embodiments, an effectiveness of the treatment may be assessed. For example, thermal imaging may be employed as a medium to verify spot-by-spot treatment application. When a spot of treatment is applied, the spot in question may be detectable on the infrared spectrum, and where a suitable thermal "uptake" is observed, such an observation may indicate that the spot size and/or depth was adequate, or too light, or too heavy. Thus, where readings returned findings that would be too light or too heavy, an adjustment for the next similar application point may be made to see maximum benefit from the treatment process upon completion. As discussed hereinabove, the effectiveness of the treatment may be assessed as well using OCT, ultrasound, and/or color.

In one embodiment a patient may undergo treatment in a prone or lying down position on a treatment bed 204, commonly used in such treatments as LASIK and other such procedures. In another embodiment, a patient may undergo a treatment in a seated position where the user employs the use of a chin rest in combination with an slit lamp apparatus (consistent with shown in the system 201 described hereinbelow).

The laser system may include at least one processor (e.g., in laser alignment and control module, in light sensing and conditioning module, or separately from both or within both); memory (e.g., in laser alignment and control module, in light sensing and conditioning module, separately from both or within both); and at least one program stored in the memory and executable by the at least one processor, the at least one program comprising instructions to perform one or more operations for improving vision using the laser system.

In one embodiment, the laser apparatus 202 may be used to obtain a predetermined pattern characterized by a plurality of positions along a plurality of spatially distributed iris tissues of an eye of a patient. Accordingly, in some embodiments, the laser system (e.g., the laser alignment and control module) may retrieve (e.g., stored in memory) or may generate a predetermined pattern including a plurality of positions along which the laser light beam from laser light source is targeted on the patient's iris. The plurality of positions may occur along spatially distributed iris tissues of the eye of the patient (e.g., the plurality of positions and the predetermined pattern).

The treatment beam 206 may be operated in accordance with one or more of the plurality of positions along a plurality of spatially distributed iris tissues. In some embodiments, a light sensing and conditioning module may be used to determine parameters specific to the patient that may determine or guide the alignment of the treatment beam 206 beam onto the patient's iris tissues. In such embodiments, light sensing and conditioning module determines (e.g., measures and/or estimates) an individual patient's eye size, iris diameter, tissue transparency, extent of pupil dilation, distance or the eye and/or iris tissue to laser light source and the like. Such light sensing and conditioning module may optionally provide a feedback signal to the laser alignment and control module so as to guide the alignment of the laser illumination light beam in accordance with one or more of the plurality of positions along a plurality of spatially distributed iris tissues on the patient's iris based on the patient-specific parameters determined by the light sensing and conditioning module. The light sensing and conditioning module may focus and guide the optical path of the laser light beam onto one or more of the plurality of positions along a plurality of spatially distributed iris tissues.

Further, the treatment beam may be delivered in a predetermined pattern on a surface of the eye of the patient; and burn (e.g., treating and/or heating to a predetermined temperature) at least a subset of the spatially distributed iris tissues, by the delivery of the laser illumination light beam in the predetermined pattern, causing the subset of iris tissues to scarify thereby resulting in a permanent decrease in diameter of the pupil of the eye. In some embodiments, by weakening or scarifying specific muscles (e.g., the dilator muscles) in the patient's iris, the capacity or ability of the respective muscles to contract is reduced causing the muscles to be limited in their ability to shorten in length (or contract).

In some embodiments, the laser light source may be a pulse laser, as discussed hereinabove, and the laser illumination light beam may comprise a sequence of a plurality of light pulses with an average repetition rate between consecutive light pulses in the plurality of light pulses that is between 2 Hertz and 100 kiloHertz. In some embodiments, a slower laser (e.g., a laser with a lower pulse repetition rate) may be used to target the inner iris or the stromal tissue and heat the tissue to cause contraction of the collagen in the stroma; when targeted on the dilator muscles, the slower laser causes weakening of the dilator muscles. In some embodiments, a faster laser (e.g., a laser with a higher pulse repetition rate, for example, used in conjunction with the predetermined pattern shown herein) may be used to target a substantial portion of the length of the iris to cut (e.g., to scarify) the collagen in the stromal tissue. In this manner, the stroma collagen, and/or the dilated tissue muscle may be affected by the treatment beam 206. Additionally, the treatment beam may comprise, but not be limited to, laser light of wavelength between 530 nanometers and 1700 nanometers.

In some embodiments, one or more laser parameters may be obtained in accordance with the obtained predetermined pattern. In some embodiments, for one or more of a wavelength of laser light beam, a pulse repetition rate of pulses of the laser light beam, a pulse duration of the pulses of the laser light beam, a duration of treatment of the spatially distributed iris tissues is different for the substantially radial predetermined pattern (e.g., as described further with reference to FIGS. 12A-12B) compared to the substantially circumferential predetermined pattern (e.g., as described further with reference to FIGS. 12A-12B), and is different for the substantially circular predetermined spot treatment pattern (e.g., as described further with reference to FIG. 16). In some embodiments, a combination of laser parameters may be used to achieve a predetermined pattern characterized by a respective combination of one or more of a substantially radial predetermined pattern, a substantially circumferential predetermined pattern, and a substantially circular predetermined spot treatment pattern (e.g., as described with reference to FIG. 15 and FIG. 17). In some embodiments, the predetermined pattern may be a closed shape around the iris.

Examples, of such closed shapes include, but are not limited to, a respective combination of one or more of a substantially radial predetermined pattern, a substantially circumferential predetermined pattern, and a substantially circular predetermined spot treatment pattern. In some embodiments, the predetermined pattern may be an open shape around the iris, meaning that, in such embodiments, the predetermined pattern does not reach all the way around the eye with respect to the iris. In fact, in some embodiments, the shape may traverse less than 90 percent, less than 80 percent, less than 70 percent, less than 60 percent, less than 50 percent, or less than 40 percent around the eye with respect to the pupil.

In such embodiments, the predetermined pattern may be a substantially radial predetermined pattern, a substantially circumferential predetermined pattern, and/or a substantially circular predetermined spot treatment pattern that traverses less than 90 percent, less than 80 percent, less than 70 percent, less than 60 percent, less than 50 percent, or less than 40 percent around the eye with respect to the pupil. In some embodiments, the predetermined pattern, while being a respective combination of one or more of a substantially radial predetermined pattern, a substantially circumferential predetermined pattern, and a substantially circular predetermined spot treatment pattern, may not cover one, two, three, four, five, six, seven, or eight or more portions of the eye radiating from the pupil.

As can be appreciated, the human eye has three layers: the sclera and cornea; the iris (on the anterior side) and the choroid (posterior); and the retina. The iris is the colored annular portion of the eye visible in the frontal view. The pupil is the dark opening in the center of the iris that permits light to enter the posterior regions of the eye. The size of the pupil opening determines the intensity of light entering the eye. The size of the pupil opening is governed by the extent of contraction of the iris muscles as explained below. The eye lens focuses the light entering through the pupil through a process known as "accommodation." The accommodation reflex may include changing the focal length of the lens via the ciliary muscles, reducing pupil size, and/or converging of the eyes. Vision defects (e.g., near-sightedness or myopia; or far-sightedness or hypermetropia; or presbyopia) are frequently corrected by the use of one or more external lenses. Altering or modifying the eye's natural "accommodation" function by targeting the ciliary muscles or the eye's natural lens may be is another method to help improve vision.

In one embodiment, vision may be improved by reducing the pupil size (which may be one of the components of accommodation). This can be achieved by reducing the pupil's ability to dilate, by affecting the iris tissues that impact the extent of pupil opening. Such methods of vision correction prevent peripheral and stray light from entering the pupil thereby reducing optical aberrations and improving visual acuity without impacting the eye's natural focusing mechanisms. The disclosed methods would help increase the depth of focus for patient's presenting with presbyopia (or any eye condition) without impacting the functioning of the natural eye lens (e.g., without impacting the eye's natural focusing process). As a result, the disclosed embodiments would help improve visual acuity at near distances in patients with presbyopia.

In some embodiments the laser apparatus may include a laser, the radiation of which is focusable as a laser illumination light beam forming a predetermined pattern characterized by a plurality of positions along a plurality of spatially distributed iris tissues of an eye of a patient. The laser apparatus may further comprise an alignment mechanism for aligning said laser illumination light beam in accordance with one or more of the plurality of positions along the plurality of spatially distributed iris tissues. The laser apparatus may also comprise a delivery mechanism for delivering said laser illumination light beam in the predetermined pattern on a surface of the eye of the patient thereby burning at least a subset of the spatially distributed iris tissues, by the delivery of the laser illumination light beam in the predetermined pattern, thereby resulting in a permanent or long term decrease in diameter of the pupil of the eye. In some embodiments, the laser may be a vertical-cavity emitting surface-emitting laser. In some embodiments, the laser may be a continuous wave laser that is pulsed. Additionally, the continuous wave laser may include an offset such that it may be used to treat below the surface. Further, the continuous wave laser may not be pulsed but may be a continuous laser.

In some embodiments, an optical amplification system may comprise an optical amplifier, the emission of which is focusable as an emission beam forming a predetermined pattern characterized by a plurality of positions along a plurality of spatially distributed iris tissues of an eye of a patient. The optical amplification system may further comprise an alignment mechanism for aligning said emission beam in accordance with one or more of the plurality of positions along the plurality of spatially distributed iris tissues. The optical amplification system may further comprise a delivery mechanism for delivering said emission beam in the predetermined pattern on a surface of the eye of the patient thereby burning at least a subset of the spatially distributed iris tissues, by the delivery of the emission beam in the predetermined pattern, thereby resulting in a permanent decrease in diameter of the pupil of the eye. In some embodiments, the optical amplifier may be a laser or photon generator.

In some embodiments, an optical amplification system may comprise an optical amplifier, the emission of which is focusable as an emission beam. The optical amplification system may further comprise at least one processor, memory, and at least one program stored in the memory and executable by the at least one processor, the at least one program comprising instructions to: obtain a predetermined pattern characterized by a plurality of positions along a plurality of spatially distributed iris tissues of an eye of a patient; align said emission beam in accordance with one or more of the plurality of positions along the plurality of spatially distributed iris tissues; deliver said emission beam in the predetermined pattern on a surface of the eye of the patient; and burn at least a subset of the spatially distributed iris tissues, by the delivery of the emission beam in the predetermined pattern, thereby resulting in a permanent decrease in diameter of the pupil of the eye. Additionally, the instructions may be used to implement the method 100.

In some embodiments, an acoustic amplification system may comprise an acoustic amplifier, the emission of which is focusable as an emission beam forming a predetermined pattern characterized by a plurality of positions along a plurality of spatially distributed iris tissues of an eye of a patient. The acoustic amplification system may further comprise an alignment mechanism for aligning said emission beam in accordance with one or more of the plurality of positions along the plurality of spatially distributed iris tissues; and a delivery mechanism for delivering said emission beam in the predetermined pattern on a surface of the eye of the patient thereby burning at least a subset of the spatially distributed iris tissues, by the delivery of the emission beam in the predetermined pattern, thereby resulting in a permanent decrease in diameter of the pupil of the eye. In some embodiments, the acoustic amplifier may include an ultrasound energy generator.

In some embodiments, an acoustic amplification system may comprise an acoustic amplifier, the emission of which is focusable as an emission beam; at least one processor; memory; at least one program stored in the memory and executable by the at least one processor, the at least one program comprising instructions to: obtain a predetermined pattern characterized by a plurality of positions along a plurality of spatially distributed iris tissues of an eye of a patient; align said emission beam in accordance with one or more of the plurality of positions along the plurality of spatially distributed iris tissues; deliver said emission beam in the predetermined pattern on a surface of the eye of the patient; and burn at least a subset of the spatially distributed iris tissues, by the delivery of the emission beam in the predetermined pattern, thereby resulting in a permanent decrease in diameter of the pupil of the eye. Additionally, the instructions may be used to implement the method 100.

It will be understood that one or more of the systems disclosed herein (e.g., the laser system, the laser apparatus 202, the treatment beam 206, the ophthalmic laser system, the ophthalmological laser system, the optical amplification system, the acoustic amplification system, and the like) are optionally fabricated to include one or more of the predetermined patterns (e.g., rather than obtaining the predetermined patterns from memory). Alternatively, or in addition, one or more of the systems described herein may be configured to retrieve one or more of the predetermined patterns from memory or generate one or more of the predetermined patterns.

In some embodiments, the predetermined pattern (e.g., of the one or more of the plurality of positions along a plurality of spatially distributed iris tissues) may include a substantially radial pattern. In such embodiments, the laser light beam may be focused on and burn (e.g., heats, scarifies and/or cuts) the iris stromal tissue and/or the iris dilator muscle tissue. In some embodiments, to produce contraction of the collagen in the stroma, the stroma may be targeted with the laser light beam. In some embodiments, to cause a weakening of the dilator muscle, the dilator muscle may be cut with or affected by the laser light beam.

In some embodiments, the predetermined pattern (e.g., of the one or more of the plurality of positions along a plurality of spatially distributed iris tissues) may include a substantially circumferential pattern. In some embodiments, the circumferential pattern is defined or formed along (e.g., proximal to) the inner circumference of the iris (e.g., external and adjacent to the sphincter muscle, for example targeting the iris stromal tissue and the iris dilator muscles). In such embodiments, the laser light beam may be focused on, and burn (e.g., heats, cuts, and/or scarifies) the iris tissue (e.g., near the iris limbus or the tissue external and adjacent to the sphincter muscle, for example targeting the iris stromal tissue and the iris dilator muscles). In some embodiments, the circumferential pattern may be defined or formed along (e.g., proximal to) the outer circumference of the iris (e.g., near the iris root). In such embodiments, the laser light beam may be focused on, and burns (e.g., heats, cuts and/or scarifies) the iris dilator muscle tissue. In some embodiments, the circumferential pattern may be any closed form pattern, or substantially closed form pattern, that includes an arcuate edge and defines two or more, three or more, four or more, five or more, or six or more positions about the pattern where a cut is to be made by a laser or other cutting instrument, such as a surgical tool.

In some embodiments, the predetermined pattern (e.g., of the one or more of the plurality of positions along a plurality of spatially distributed iris tissues) may include a substantially circular spot pattern. In some embodiments, the substantially circular spot pattern may be formed along (e.g., proximal to) the inner circumference of the iris (e.g., external and adjacent to the sphincter muscle, for example targeting the iris stromal tissue and the iris dilator muscles). In such embodiments, the laser light beam is focused on, and burns (e.g., heats, cuts, and/or scarifies) the iris tissue (e.g., near the iris limbus or the tissue external and adjacent to the sphincter muscle, for example targeting the iris stromal tissue and the iris dilator muscles). In another embodiment, if the sphincter were subject of the treatment, the power and time may be modified (e.g. decreased power and longer time for treatment).

In some embodiments, the predetermined pattern (e.g., of the one or more of the plurality of positions along a plurality of spatially distributed iris tissues) may include a combination of two or inure of a substantially radial pattern, a substantially circumferential pattern, and a substantially circular spot pattern. In such embodiments, the laser light beam may be focused on, and burn (e.g., heats, cuts, and/or scarifies) one or more of: the iris dilator muscle tissue, the iris limbus tissue (e.g., external and adjacent to the sphincter muscle, for example targeting the iris stromal tissue and the iris dilator muscles), and the iris stromal tissue.

It is to be appreciated that although the predetermined patterns disclosed herein may be used, an emphasis of improvements in the modulating laser treatment system include a patient and eye-specific pattern that is created for purposes of treating the eye. As such, the predetermined patterns disclosed herein may be used independent or in combination with the patient and eye-specific pattern detailed herein.

Figure 2B:
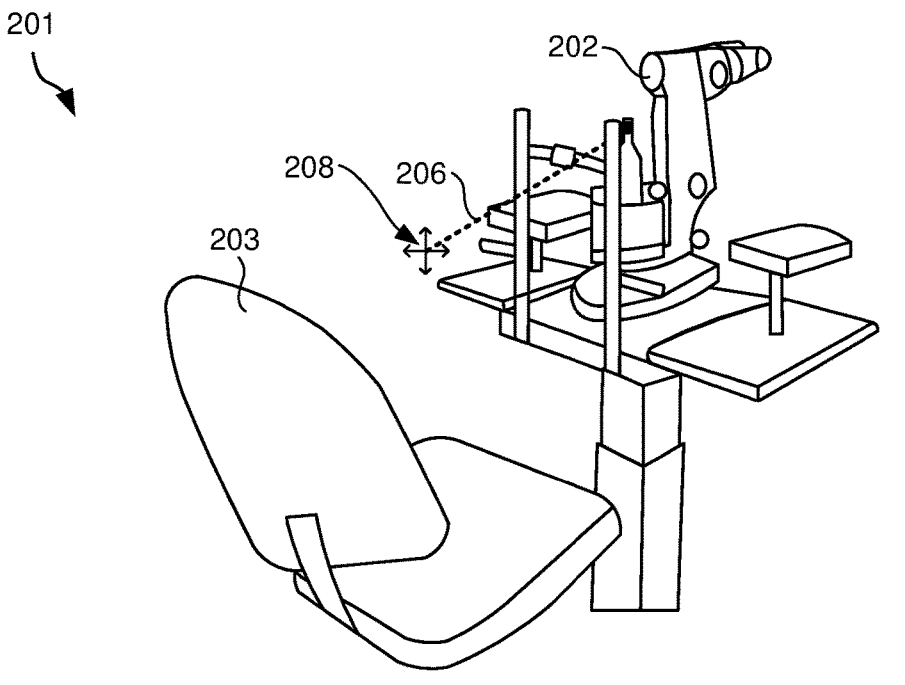
FIG. 2B illustrates an exemplary modulating laser treatment system, in accordance with one embodiment.

FIG. 2B illustrates an exemplary modulating laser treatment system 201, in accordance with one embodiment. As an option, the system 201 may be implemented in the context of any one or more of the embodiments set forth in any previous and/or subsequent figure(s) and/or description thereof. Of course, however, the system 201 may be implemented in the context of any desired environment. Further, the aforementioned definitions may equally apply to the description below.

As shown, the system 201 may be comprised of a laser apparatus 202, a patient treatment chair 203, a laser treatment beam 206, and the ability to modulate the direction of the treatment beam 208. It is to be appreciated that the system 201 represents just one configuration, and that other alterations (i.e. small-form, transportable, etc.) are envisioned. Thus, the system 201 may operate in a similar manner to the system 200, with the primary distinction being that the patient is treated upright (in system 201) as opposed to lying down (in system 200).

In one embodiment, the laser apparatus 202 of the system 201 may include a yttrium aluminum garnet (YAG) laser or continuous wave laser. Additionally, the laser treatment beam 206 may be provided using a slit lamp associated with the laser apparatus 202. In another embodiment, the laser apparatus 202 of the system 201 may include a Diode laser.

Further, it is to be understood that the system 200 and/or the system 201 may configured to be a permanently installed system, and/or may be a portable system.

FIG. 2C illustrates a close up view 205 of the iris, in accordance with one embodiment. As an option, the close up view 205 may be implemented in the context of any one or more of the embodiments set forth in any previous and/or subsequent figure(s) and/or description thereof. Of course, however, the close up view 205 may be implemented in the context of any desired environment. Further, the aforementioned definitions may equally apply to the description below.

As shown, the close up view 205 of the iris includes a mapping of the iris, including an anterior surface 214 (the surface that faces outward), a posterior surface 222 (the surface that faces inward), iris limbus 210 (region between the transparent cornea and opaque sclera), sphincter 218 (muscle that encircles the pupil of the eye), stroma 212

(fibrovascular layer of tissue in the iris), dilator 220 (muscle running radially in the iris), and an iris root 216 (outer edge of the iris).

FIG. 3 illustrates a block diagram 300 illustrating the modulating laser treatment system, in accordance with one embodiment. As an option, the block diagram 300 may be implemented in the context of any one or more of the embodiments set forth in any previous and/or subsequent figure(s) and/or description thereof. Of course, however, the block diagram 300 may be implemented in the context of any desired environment. Further, the aforementioned definitions may equally apply to the description below.

In one embodiment, modulated treatment may take place on a spot-by-spot basis. Thus, in one example, an active OCT may be connected to the user's laser delivery slit lamp viewing device during the procedure, where the OCT may then be able to determine whether the last treatment spot was of the appropriate depth (not too deep or too shallow) and dense enough in delivery to produce the desired treatment result. In other embodiments, ultrasound, thermal imaging, etc. may be used to also determine the effectiveness of the treatment.

As shown, the block diagram 300 is a block diagram illustrating a laser system in accordance with one embodiment of the present invention. The laser system may include one or more processing units (CPU's) 302 for executing modules, programs and/or instructions stored in memory 310 and thereby performing processing operations; one or more network or other communications interfaces 304; memory 310; and one or more communication buses 314 for interconnecting these components. The communication buses 309 optionally include circuitry (sometimes called a chipset) that interconnects and controls communications between system components. The ophthalmic laser system 100 optionally may include a user interface 305 comprising a display device 306 and an input device 308. Laser 374 includes one or more discrete laser light sources (e.g., with one or more wavelengths of pulse laser output) that is used to generate the laser light beam directed onto the surface of the patient's iris.

Optical conditioning elements 370 optionally include optical assembly and components to focus, align, and condition the laser light beam generated by laser 371. Memory 310 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 310 may optionally include one or more storage devices remotely located from the CPU(s) 302. Memory 310, or alternately the non-volatile memory device(s) within memory 310, comprises a non-transitory computer readable storage medium.

In some embodiments, memory 310, or the computer readable storage medium of memory 310 stores the following programs, modules and data structures, or a subset thereof: an operating system 312 that includes procedures for handling various basic system services and for performing hardware dependent tasks; a network communication module 311 that is used for connecting the ophthalmic laser system 100 to other computers via the one or more communication network interfaces 309 (wired or wireless) and one or more communication networks, such as the Internet, other wide area networks, local area networks, metropolitan area networks, and so on; a user interface module 316 that receives commands from the user via one or more input devices 308 of user interface 305, generates user interface objects in display device 306, and/or a visual representation of the patient's iris or other parts of the patient's eye, a representation of one or more of the predetermined patterns superimposed on the visual representation of the patient's iris.

The user interface module 316 optionally facilitates the alignment of laser light beam on specific portions of the patient's iris; a laser alignment module 318 that provides commands to align a laser light beam in accordance with a selected predetermined pattern and optionally guides the laser light beam along the plurality of positions along the spatially distributed iris tissues that characterize the predetermined pattern; a laser delivery module 320 that includes control instructions and commands to operate laser 374 to produce laser light beam that is optionally directed through optical conditioning elements 370 to be incident on the patient's iris; predetermined patterns 322 that include multiple sets of predetermined patterns (stored, for example, in a database of predetermined patterns) that correspond to a plurality of positions along a plurality of spatially distributed iris tissues along which the laser beam is aligned (e.g., by the laser alignment module 318) for vision treatment or vision improvement; laser parameters 324 are sets of parameters (e.g., wavelength of laser light, average pulse duration, average pulse repetition rate, average treatment time, average treatment temperature or range of temperature increase of tissue, laser peak power, laser pulse energy, and the like) are optionally selected in accordance with the selected predetermined pattern from the predetermined patterns 322 for vision treatment or vision improvement; and patient parameters 326 are sets of parameters (e.g., iris dimensions-inner and outer circumferences of the iris and iris thickness, extent of pupil dilation, pupil diameter, distance of treatment area from the laser source, and the like) that are specific to individual patients and are optionally used to determine the predetermined pattern and the laser parameter used for vision treatment or vision improvement.

Figure 7:
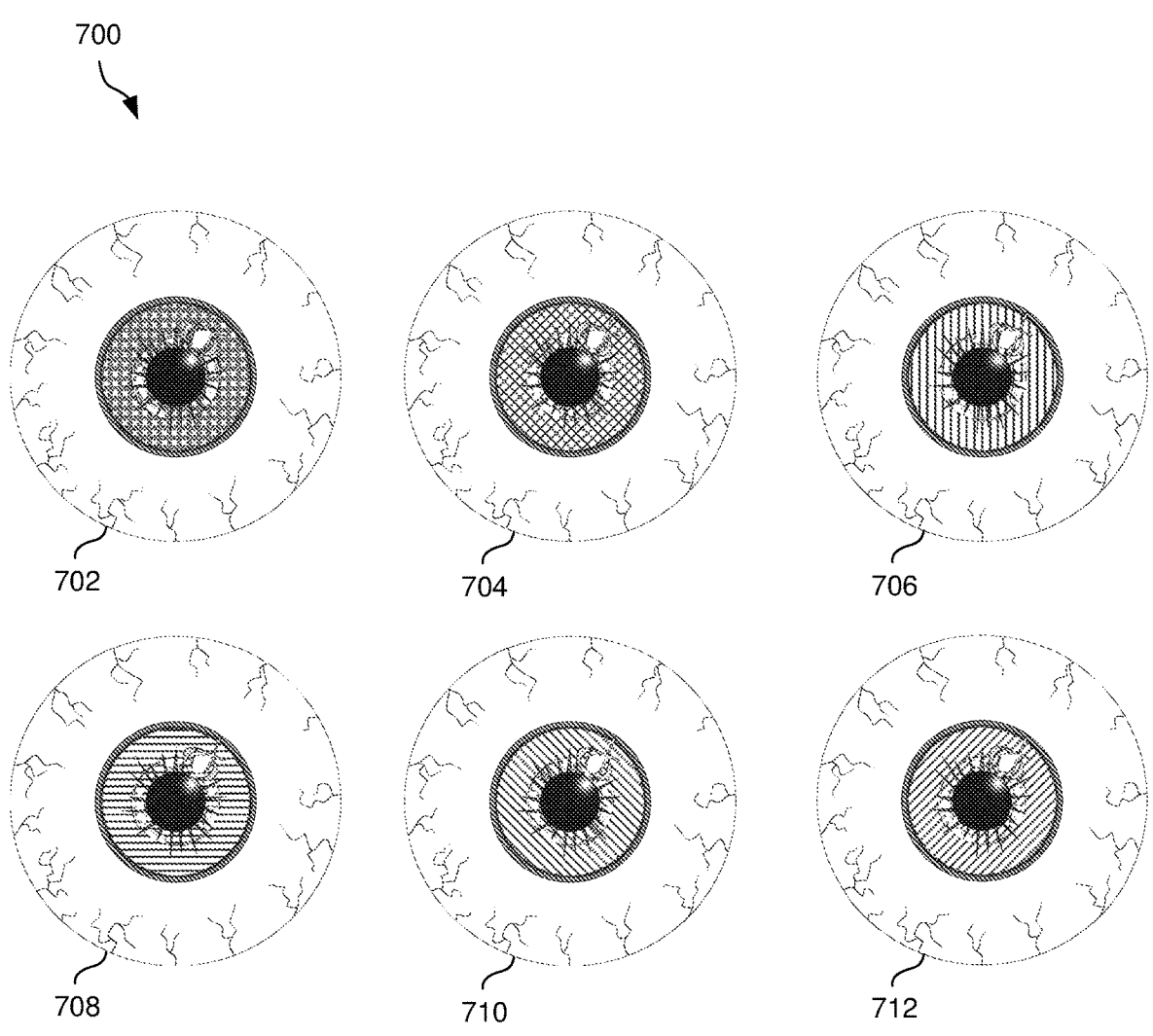
FIG. 7 illustrates a color mapping of the eye, in accordance with one embodiment.

In other embodiments, memory 310, or the computer readable storage medium of memory 310 stores the following programs, modules and data structures, or a subset thereof: an eye map 328 of the patient resulting from an eye mapping operation; a depth map 330 (consistent with operation 104); a color map 332 based on color mapping of the eye (consistent with FIG. 7 provided herein); a calculation of the necessary laser offset 334 to facilitate laser treatment in accordance with the modulated treatment; a record of the patient's eye tracking 336 while delivering the laser illumination light beam(s); and a record of eye feedback 338 (and/or real-time measurements of the positioning of the eye) and the respective degrees of effect for each instance of feedback recorded to guide the alignment of the laser illumination light beam during a procedure.

Each of the above identified elements may be stored in one or more of the previously mentioned memory devices, and corresponds to a set of instructions for performing a function described above. The above identified modules or programs (i.e., sets of instructions) need not be implemented as separate software programs, procedures or modules, and thus various subsets of these modules may be combined or otherwise re-arranged in various embodiments. In some embodiments, memory 310 may store a subset of the modules and data structures identified above. Furthermore, memory 310 may store additional modules and data structures not described above.

Although the block diagram 300 shows a laser system, it is to be appreciated that the block diagram 300 is intended more as functional description of the various features which may be present in a set of servers than as a structural schematic of the embodiments described herein. In practice, and as recognized by those of ordinary skill in the art, items shown separately could be combined and some items could be separated. For example, some items shown separately in the block diagram 300 could be implemented on single servers and single items could be implemented by one or more servers. The actual number of servers used to implement an ophthalmological laser system and how features are allocated among them will vary from one implementation to another.

Figure 4:
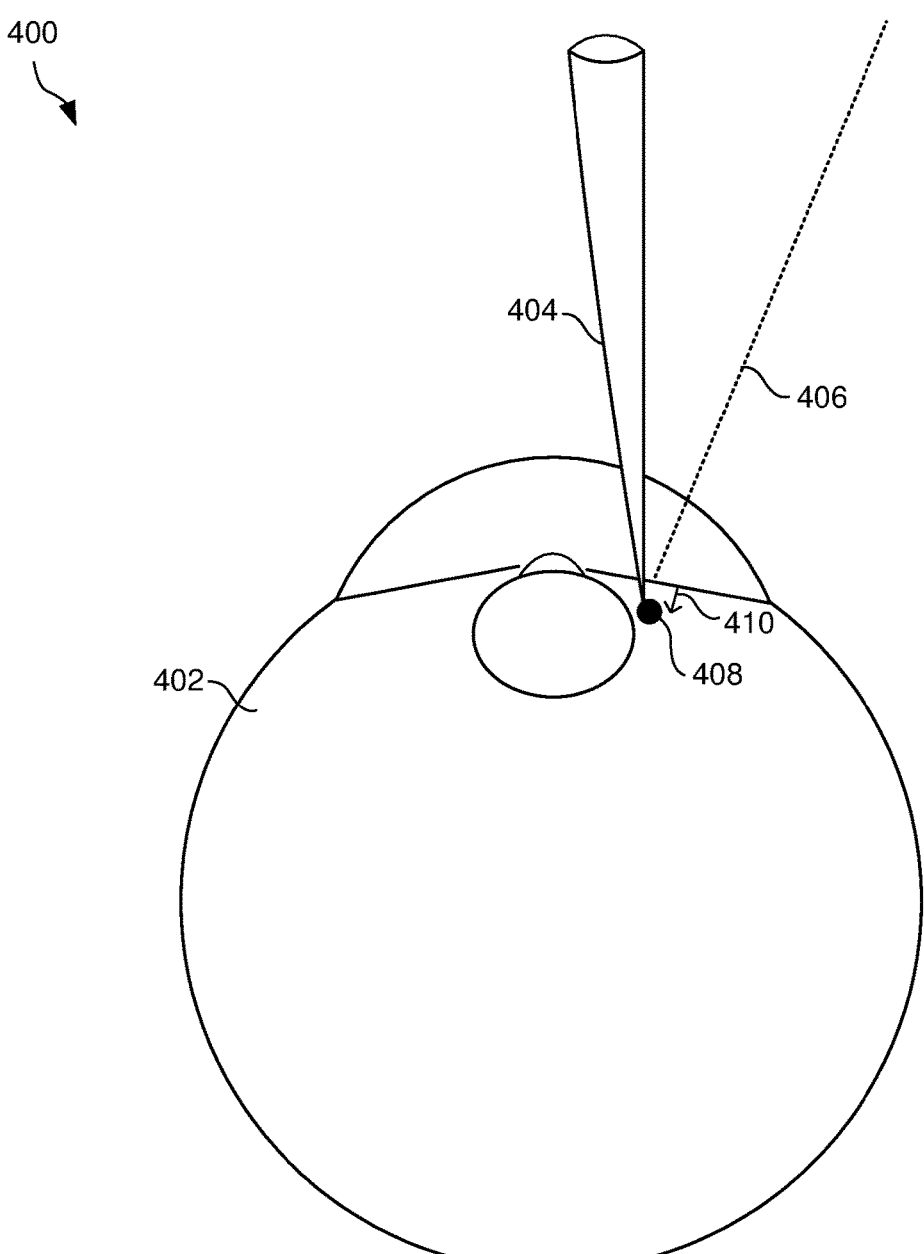
FIG. 4 illustrates a laser offset treatment, in accordance with one embodiment.

FIG. 4 illustrates a laser offset treatment 400, in accordance with one embodiment. As an option, the laser offset treatment 400 may be implemented in the context of any one or more of the embodiments set forth in any previous and/or subsequent figure(s) and/or description thereof. Of course, however, the laser offset treatment 400 may be implemented in the context of any desired environment. Further, the aforementioned definitions may equally apply to the description below.

As shown, the laser offset 400 depicts a simple representation of an eye 402. Additionally, the laser offset treatment includes a first laser beam 404 and a second laser beam 406. Further, the laser offset 400 depicts the resulting offset laser point 408 based on the first laser beam 404 and the second laser beam 406. Further still, the laser offset 400 includes a distance 410 between the first laser beam 404 and the second laser beam 406.

Additionally, the laser offset 400 may include the distance (in depth of treatment of the iris) between the second laser beam 406 (aiming beam) and the focus of the first laser beam 404 (treatment beam). The second laser beam 406 (aiming beam) may be focused on the anterior surface of the iris, while the first laser beam 404 (treatment beam) may be 50 to 250 microns deeper. In one exemplary setup both the second laser beam 406 (aiming beam) and the first laser beam 404 (treatment beam) follow the same optical path through the system. Further, the color of second laser beam 406 (aiming beam) may be green or red or some other color. The color of the first laser beam 404 (treatment beam) may be infrared.

Further, a beam angle may refer to the narrowing of the angle (of either or both of the first laser beam 404 and/or the second beam 406) as it reaches its focal point (such as the offset laser point 408). In one embodiment, treatment of the iris may occur at a setting perpendicular to the iris for maximum effect (although this may be altered to reach the desired location in the iris).

In operation, the laser point 408 may be modified by manipulating the first laser beam 404 and/or the second laser beam 406. In this manner, the laser offset 400 may enable treatment of the anterior layers (i.e. layers below the surface) of the iris, and/or other parts of the eye.

In one embodiment, the first laser beam 404 may be a treatment and the second laser beam 406 may be a focusing beam (or guiding beam, aiming beam). In one embodiment, both the first laser beam 404 and the second laser beam 406 may each be of a conical shape (or a 3d cone shape, converging beam, etc.). In use, the second laser beam 406 may be focused on the surface of the tissue of the iris, and the first laser beam 404 may, in turn, converge at the distance 410 below the focus point of the second laser beam 406. In one embodiment, the distance 410 may be a function of the thickness of the iris. Additionally, the offset (how far beyond the first laser beam 404 penetrates past the anterior surface of the iris) may be changed based on prior treatment. For example, the laser point 408 may be determined to be at a first depth which was not as effective as desired. Thus, the laser point 408 may be altered (lesser/greater depth) by changing the first laser beam 404 to treat the iris and/or the second laser beam 406 (to aim where to treat the iris) at a subsequent location.

In one embodiment, the first laser beam 404 may be used to treat the dilator muscles associated with the iris. Still yet, in one embodiment, the first laser beam 404 and/or the second laser beam 406 may be an infrared laser.

In one embodiment, the laser offset 400 may be used in the context of a continuous wave laser manipulated through the optical pathway to the varying locations and depths of a patient's iris. In one application, one or more helium neon beams may focus on a single point upon or within the iris and deliver a laser treatment application point thereto. This treatment process may be then repeated as necessary to achieve the ultimate treatment result desired for the patient in question. The laser may also be employed in a continuous wave format where the laser burn is initiated and the delivery site is moved to various locations without pulses in a continuous line. Thus, in this manner, the continuous wave format may be a continuous delivery of the laser beam to the eye.

FIG. 5 illustrates a laser offset treatment 500 at multiple eye positions, in accordance with one embodiment. As an option, the laser offset treatment 500 may be implemented in the context of any one or more of the embodiments set forth in any previous and/or subsequent figure(s) and/or description thereof. Of course, however, the laser offset treatment 500 may be implemented in the context of any desired environment. Further, the aforementioned definitions may equally apply to the description below.

As shown, the laser offset treatment 500 depicts multiple simple representation of an eye. Laser beam angles may change depending on the position of the eye 502. For example, first laser point 504 may be associated with a first beam angle and a second beam angle, second laser point 506 may be associated with a third beam angle and a fourth beam angle, and third laser point 508 may be associated with a fifth beam angle and a sixth beam angle. These laser beam angles associated with each of the first laser point 504, the second laser point 506, and the third laser point 508 may change as the eye 502 may shift (and/or otherwise move). This shifting may be shown in time graph 510 where each of the first laser point 504, the second laser point 506, and the third laser point 508 are plotted with respect to time.

In this manner, as the eye may shift, the laser offset treatment 500 may account for the change in position of the laser point. To be clear, the laser point (i.e. the point at which laser treatment is to be applied), does not change but remains constant, while the angles of the laser beams may change in order to hit the intended laser point notwithstanding movements of the eye.

Additionally, although not shown, the laser beams may be modified to not only account for movement of the eye (and corresponding changes in laser beam angles), but may also be modified to account for various laser points (at varying depths).

FIG. 6 illustrates a method 600 for guiding treatment based on a mapping of the eye, in accordance with one embodiment. As an option, the method 600 may be implemented in the context of any one or more of the embodiments set forth in any previous and/or subsequent figure(s) and/or description thereof. Of course, however, the method 600 may be implemented in the context of any desired environment. Further, the aforementioned definitions may equally apply to the description below.

As shown, the method 600 comprises scanning a patient's eye. See operation 602. Next, a mapping is created of the eye including thickness, color, and location conditions. See operation 604. For example, consistent with the discussion herein, the mapping may correspond with the operation 104. Such mapping may include any characteristic of the eye, including but not limited to thickness, position(s), contour(s), topology, dimensions(s), 2d representation, 3d representation, etc.

Further, it is determined whether the patient's eye has moved. See decision point 606. If it has moved, the mapping is recalibrated. See operation 608. Recalibration may include modifying in some manner the offset laser points, the laser beam angles, the power of the laser beam, the wattage of the laser beam, the depth of the laser point, etc.

Further still, if the eye has not moved per decision 606, treatment is guided based on the mapping of the eye. See operation 610. As discussed herein, such mapping may include a patient and eye-specific pattern.

In one embodiment, the physician may employ a diagnostic element of a process (tracking movement, verifying individual treatment points) at the same time as guiding the treatment via the power applied by the laser itself and making necessary adjustments during the procedure to ensure optimal treatment results. For example, the eye tracking aspect may include any number of verifications per second (including but not limited to 1000 checks per second), which in turn may cause hundreds of adjustments per second in an effort to keep the device lined up with the patient's eye to cause an effective and accurate treatment. Therefore, when making adjustments to a modulating treatment procedure, multiple "verification points" (such as those which may result from the scanning and mapping of the eye) may be employed over the course of a modulating treatment whereby the laser power and depth and location of offset may be adjusted as necessary during events where the eye has moved slightly and/or there are perceived differences in the thickness of the patient's iris under treatment.

FIG. 7 illustrates a color mapping of the eye 700, in accordance with one embodiment. As an option, the color mapping of the eye 700 may be implemented in the context of any one or more of the embodiments set forth in any previous and/or subsequent figure(s) and/or description thereof. Of course, however, the color mapping of the eye 700 may be implemented in the context of any desired environment. Further, the aforementioned definitions may equally apply to the description below.

As shown, the color mapping of the eye 700 depicts multiple color representations, including eye color 1 702, eye color 2 704, eye color 3 706, eye color 4 708, eye color 5 710, and eye color 6 712. It is to be appreciated that any number of eye colors (including a crossing or gradient from one known color to another) may be provided. Such color mappings may be used to retrieve a predetermined optimized set of instructions for the laser apparatus. For example, in response to determining that an eye has the eye color 1 702, the system may determine that for such eye color 1 702, a predetermined and preconfigured optimized wavelength and/or power settings may be associated with the eye color 1 702.

Additionally, although not shown in the color mapping of the eye 700, such color mappings may be used in combination with the eye mapping (consistent with the operation 104) such that in addition to determining a color appropriate treatment (including an optimized wavelength and/or power setting), the system may also take into consideration the intended depth of laser point for the desired treatment. In other words, color determination of the eye may be used to retrieve a set of apparatus configuration instructions, which, in turn, may be modified as needed to account for proper depth, eye shape, eye contours, and/or any other mapping information associated with the eye.

FIG. 8 illustrates a table 800 of eye color correlations, in accordance with one embodiment. As an option, the table 800 may be implemented in the context of any one or more of the embodiments set forth in any previous and/or subsequent figure(s) and/or description thereof. Of course, however, the table 800 may be implemented in the context of any desired environment. Further, the aforementioned definitions may equally apply to the description below.

As shown, the table 800 of eye color correlations includes a first column 802 representing a variety of predetermined eye color options and a second column 804 with corresponding laser predefined instructions for laser treatment based on desired eye color. The eye mapping may be automated or may involve manually mapping with color of the eye overall or at specific locations around the eye. One such iteration would be a viewing or treatment lens placed on the eye with various colors represented in the periphery of the lens which could be matched to the patient's iris color.

The table 800 may represent predefined instructions associated with the eye color 802. Such predefined instructions may be used for eye treatment (as discussed hereinabove). Additionally, however, such predefined instructions of the second column 804 may be used to physically change a color of an eye.

For example, a patient may desire to alter the natural color of their iris for some cosmetic and/or physiological reasons. In such a case, iris color may be tuned to coincide with a particular style of dress and/or other fashion-oriented accessories. To that end, achieving a different color iris may require applying different levels of laser power during iris treatment, as an iris treatment is dependent upon different absorption rates of laser application points by irises of different depths, consistencies, and thicknesses in various patients. In another embodiment, the anatomical and/or cellular make-up of the patient's iris in question may dictate an optimal (or effective) alteration in color. Additionally, the current color of the eye and the final (or desired) color of the eye (in terms of start and end points) may be used to determine an appropriate set of instructions for changing an individual's current color of the eye to the desired color.

Additionally, as can be appreciated, to cause an effective change in color, in addition to have preconfigured system instructions (for the laser), the modulating treatment may take into account other characteristics (e.g. shape, contour, depth, etc.), as discussed herein. In other embodiments, the change in color to the eye may be a temporary change (i.e. the laser treatment may cause a permanent dilatory muscle effect but a temporary color effect). For example, after treating the eye, the eye may have a color-change, but such color-change may go away (within a few days, a week, etc.) due to the small area treated with the laser.

Further, as shown on the spectrum 806, the eye color may be associated with a melanin concentration, and a correlation may exist between a determined melanin concentration and a laser instruction. For example, the laser instruction may include a change in pulse duration, an intended depth (such as the laser offset discussed herein), and/or a laser power. In one embodiment, the greater the concentration of melanin, the higher the power which may be required to penetrate the iris. It should be understood that the spectrum 806 may also represent gradients from one color to another (as the eye color may be a function of the concentration of melanin).

Figure 9:
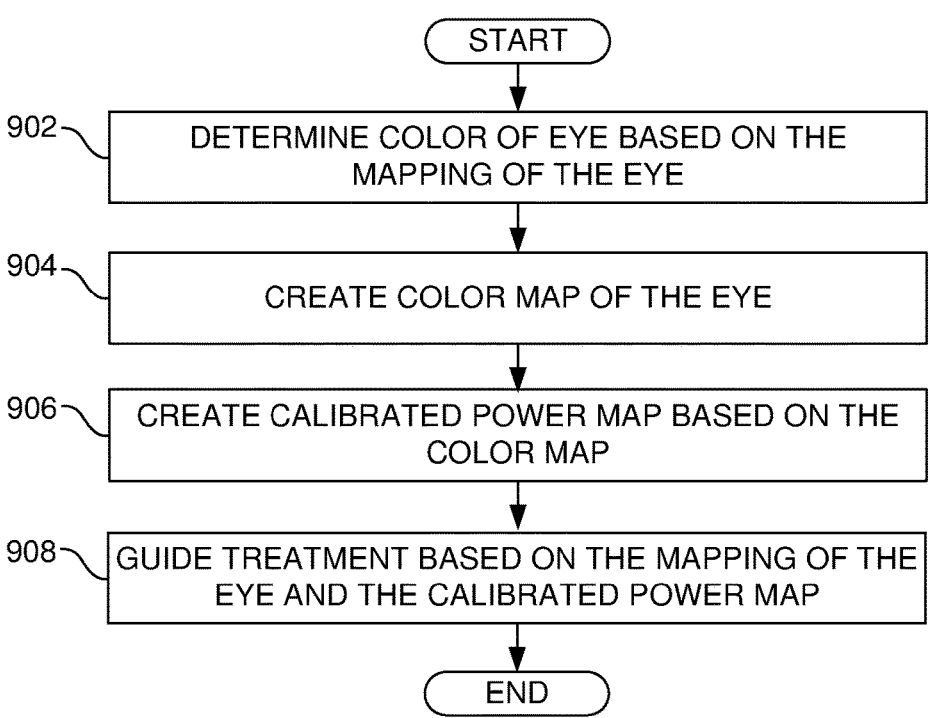
FIG. 9 illustrates a method for guiding treatment based on a mapping of the eye and a calibrated power map, in accordance with one embodiment.

FIG. 9 illustrates a method 900 for guiding treatment based on a mapping of the eye and a calibrated power map, in accordance with one embodiment. As an option, the method 900 may be implemented in the context of any one or more of the embodiments set forth in any previous and/or subsequent figure(s) and/or description thereof. Of course, however, the method 900 may be implemented in the context of any desired environment. Further, the aforementioned definitions may equally apply to the description below.

As shown, the method 900 comprises determining eye color based on mapping the patient's eye. See operation 902. Additionally, a color map is created of the patient's eye. See operation 904. Further, a calibrated power map may be created based on the color map 904. See operation 906. In addition, the treatment of the eye may be guided based on the mapping of the eye and the calibrated power map. See operation 908.

As an example, if a patient's eye has a color gradient (darker towards the center of the eye and lighter towards the outside of the eye or circumferential changes in color) or any color variation, such mapping may be used to create a corresponding power (or laser instructions) based on the preconfigured instructions that take into account the color of the eye. In this manner, the color determined may be spot-specific on the eye and may dictate a spot-specific set of instructions. Additionally, such spot-specific instructions may take into consideration other characteristics (e.g. shape, contour, depth, etc.), as discussed herein.

Figure 10:
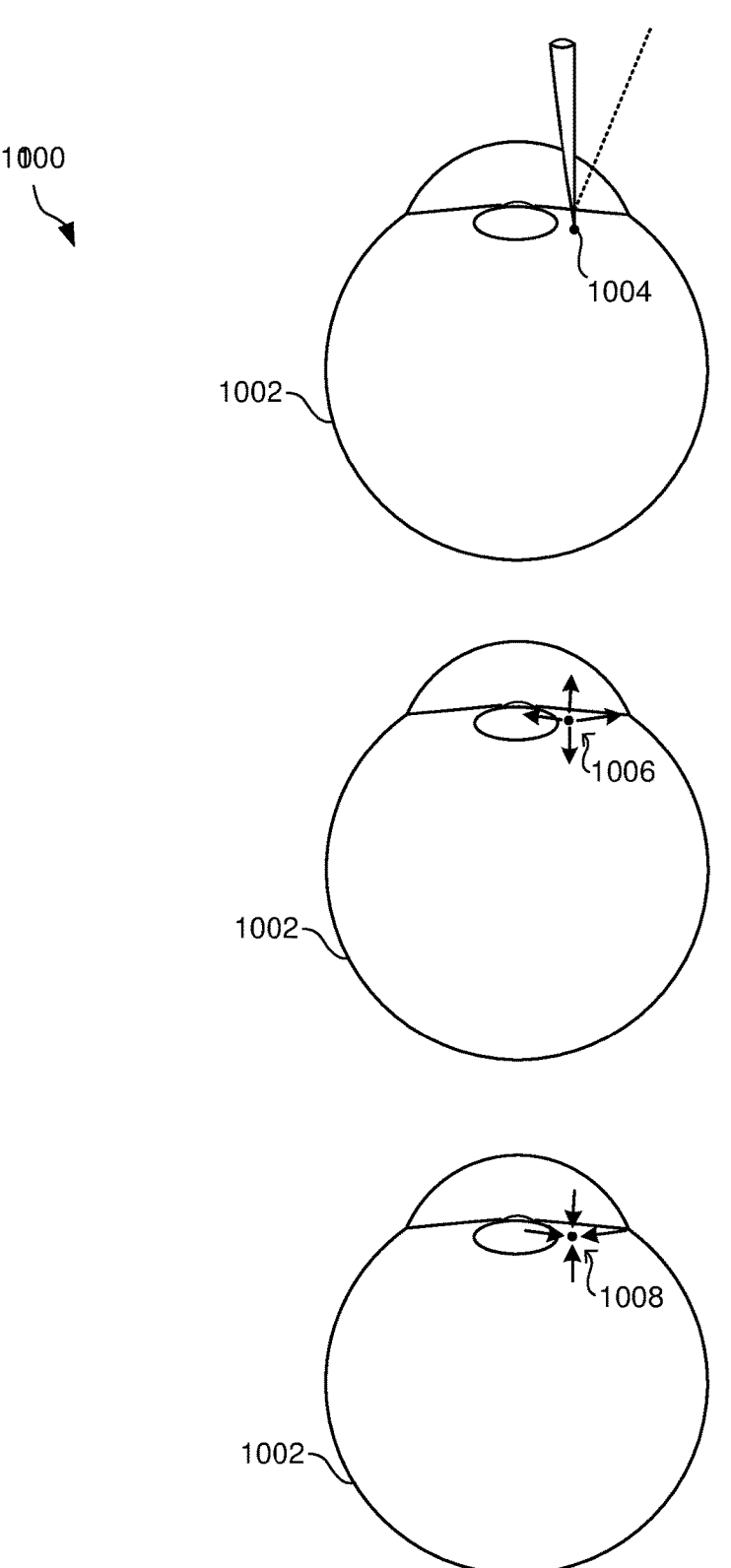
FIG. 10 illustrates eye muscle responses, in accordance with one embodiment.

FIG. 10 illustrates eye muscle responses 1000, in accordance with one embodiment. As an option, the eye muscle responses 1000 may be implemented in the context of any one or more of the embodiments set forth in any previous and/or subsequent figure(s) and/or description thereof. Of course, however, the eye muscle responses 1000 may be implemented in the context of any desired environment. Further, the aforementioned definitions may equally apply to the description below.

As shown, the eye muscle responses 1000 depicts multiple simple representation of an eye 1002. Additionally, at laser point 1004, an offset laser point treatment event is depicted. Further, a first eye muscle response may be of a first type 1006 which may in the form of the iris momentarily expanding as a direct result of the laser point event 1004. In addition, a second eye muscle response may be of a second type 1008 in the form of the iris momentarily contracting and/or shrinking as a direct result of the laser point event 1004. In another embodiment, another marker for strength of iris treatment may be visible or measured changes in iris color at the location of the laser spot delivery. Such changes may be long term or transient. In any case, a change in color may be indicative of the effectiveness of the treatment. For example, the color of the eye (including the iris) may lighten or darken as a result of the treatment. Additionally, as indicated herein, the color change may be permanent or transient.

Regardless of whether the eye muscle response is of the first type 1006, the second type 1008, and/or any other type of muscle response, the effectiveness of the laser treatment may be ascertained by determining whether a muscle response occurs. In the event a muscle response occurs, it may be determined that the laser treatment is effective. In contrast, should no muscle response occur (or below a predetermined threshold), the modulated treatment may be modified to cause a muscle response. Additionally, a sub threshold treatment could be delivered after the threshold for laser response is determined. In another embodiment, an eye response may be determined by measuring eye electrical activity (via, for example, an EMG). In this manner, electrical eye activity may be determined for purposes of determining an effective laser treatment. Similar to an eye muscle response, with respect to measuring electrical activity, should no electrical response occur (or below a predetermined threshold), the modulated treatment may be modified to cause an electrical response.

Further, in one embodiment, the eye muscle response may include collagen contracting within the iris in response to the laser point event 1004.

Figure 11:
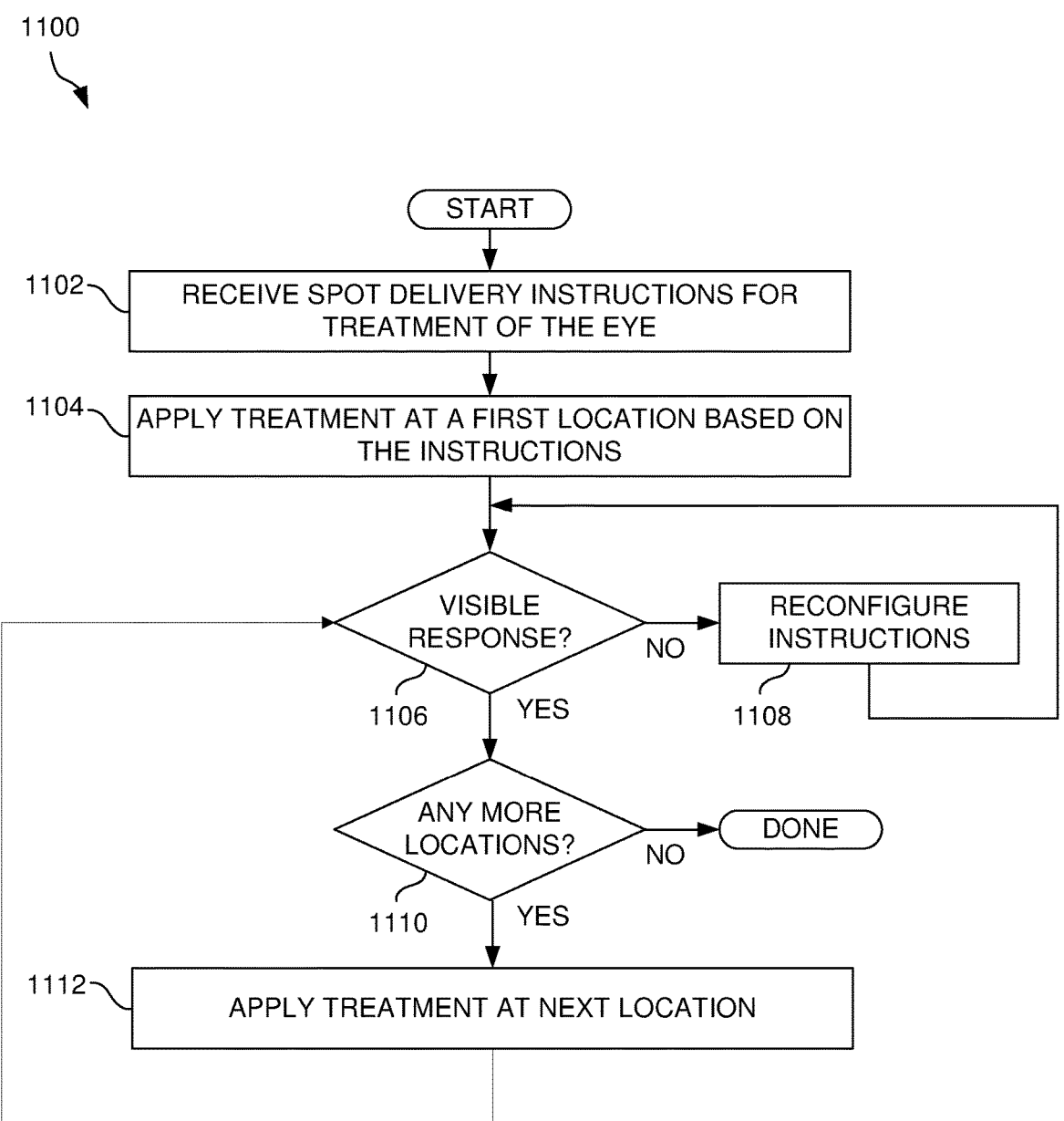
FIG. 11 illustrates a method for applying treatment based on a visible response, in accordance with one embodiment.

FIG. 11 illustrates a method 1100, in accordance with one embodiment. As an option, the method 1100 may be implemented in the context of any one or more of the embodiments set forth in any previous and/or subsequent figure(s) and/or description thereof. Of course, however, the method 1100 may be implemented in the context of any desired environment. Further, the aforementioned definitions may equally apply to the description below.

As shown, the method 1100 comprises receiving spot delivery instructions for treatment of the eye. See operation 1102. Additionally, the treatment is applied at a first location based on the instructions. See operation 1104. Further, it is determined whether there is a visible response to the treatment. See decision point 1106. As discussed within the context of FIG. 10, such visible response may include an eye muscle response. Additionally, as discussed, electrical activity may be measured to determine a response.

In addition, when a response is not ascertained, the instructions to the laser may be reconfigured. See operation 1108. For example, the modulated treatment may be updated (per operation 110) to account for the reconfiguration needed.

Further still, it is determined whether any more locations are still to receive treatment based on the instructions. See decision point 1110. For example, the locations may be consistent with a pattern (either predetermined or patient and eye-specific). Such locations may correspond with individual spot delivery locations. In the event that all spot locations have received treatment, the method 1100 is done. If not all spot locations have received treatment, treatment is applied to the next known location (consistent with the instructions of the modulated treatment). See operation 1112. Additionally, the spots may overlapped, and/or treated multiple times in the same spot with varying intervals between spots.

Figure 12A:
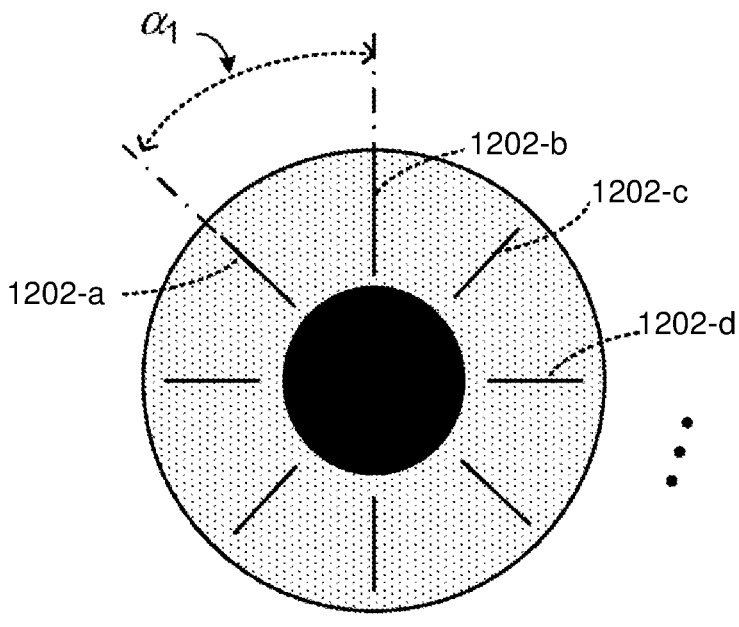
FIGS. 12A-12B illustrate substantially radial predetermined patterns of positions for delivering the laser light beam on one or more of the iris tissues of a patient's eye, in accordance with one embodiment.
Figure 12B:
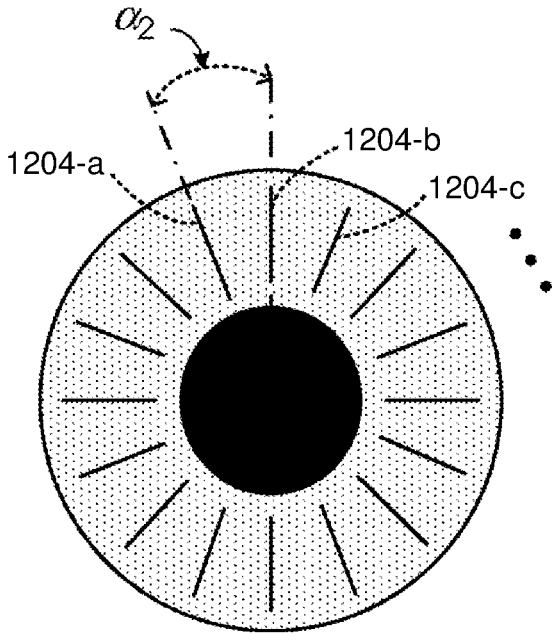

FIGS. 12A-12B illustrate substantially radial predetermined patterns of positions for delivering the laser light beam on one or more of the iris tissues of a patient's eye, in accordance with one embodiment. As an option, the patterns of positions may be implemented in the context of any one or more of the embodiments set forth in any previous and/or subsequent figure(s) and/or description thereof. Of course, however, the patterns of positions may be implemented in the context of any desired environment. Further, the aforementioned definitions may equally apply to the description below.

In some embodiments, the predetermined pattern may be a substantially radial pattern. The plurality of positions comprises N positions (e.g., positions 1202-*a*, 1202-*b*, 1202-*c*. 1202-*d* and the like where N=8 as shown in FIG. 12A; positions 1204-*a*, 1204-*b*, 1204-*c*, and the like where N=16 as shown FIG. 12B), each of the N positions oriented radially from the inner circumference (e.g., from the iris limbus; external and adjacent to the sphincter muscle, for example targeting the iris stromal tissue and/or the iris dilator muscles) of the iris proximal to the pupil to the outer circumference (e.g., the iris root) of the iris distal to the pupil. The N positions include a first position (e.g., position 1202-*a*; position 1204-*a*) and a second position (e.g., position 1202-*b*; position 1204-*b*) adjacent to the first position and separated from the first position by a predefined angular separation (e.g., positions 1202-*a* and 1202-*b* are separated by the predefined angular separation α1 of approximately 45° as shown in FIG. 12A; positions 1204-*a* and 1204-*b* are separated by the predefined angular separation α2 of approximately 22.5° as shown in FIG. 12B). In some embodiments, each position of the plurality of positions corresponds to a treatment zone (e.g., a cut) on the patient's iris using the laser light beam.

In some embodiments, the predefined angular separation has a value between 10° and 50° and N is a positive integer of value between 4 and 36. In some embodiments, an average length of the plurality of positions (e.g., or cuts or treatment zones) has a value between 1 mm and 3 mm. In some embodiments, an average thickness of the plurality of positions (e.g., or cuts or treatment zones) has a value between 10 microns and 200 microns. In some embodiments, the laser light beam is focused on the plurality of positions, thereby causing scarification of the iris stromal tissue.

Figure 13A:
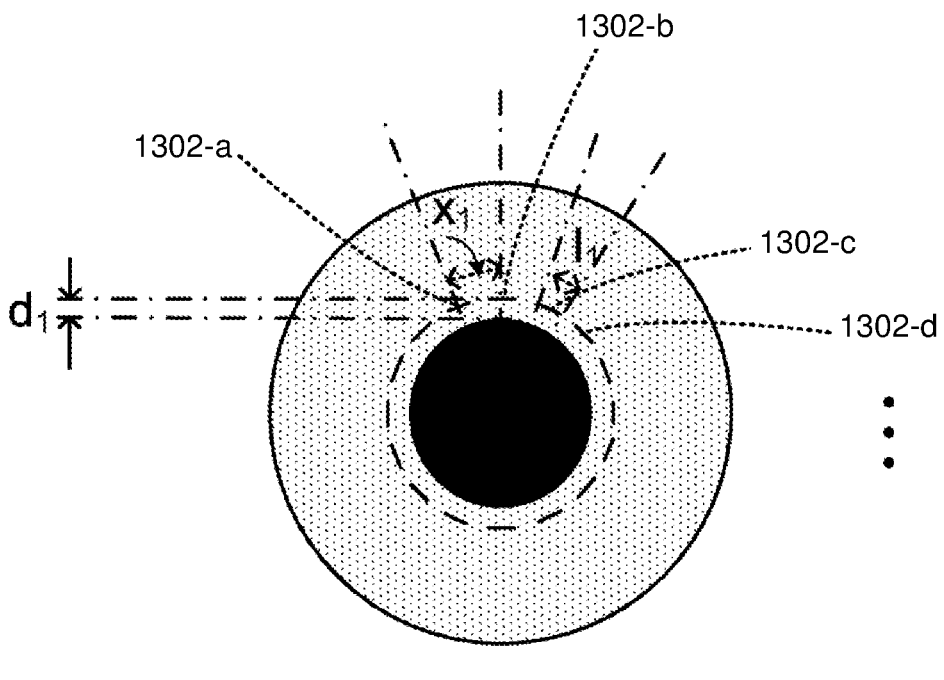
FIGS. 13A-13B illustrate substantially circumferential predetermined patterns of positions for delivering the laser light beam on one or more of the iris tissues of a patient's eye, in accordance with one embodiment.
Figure 13B:
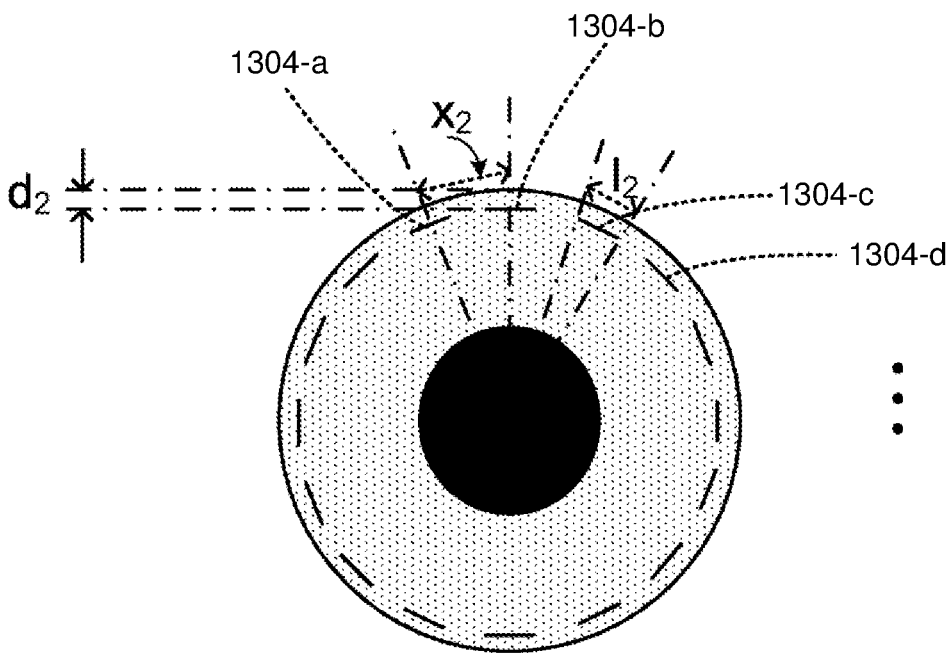

FIGS. 13A-13B illustrate substantially circumferential predetermined patterns of positions for delivering the laser light beam on one or more of the iris tissues of a patient's eye, in accordance with one embodiment. As an option, the patterns of positions may be implemented in the context of any one or more of the embodiments set forth in any previous and/or subsequent figure(s) and/or description thereof. Of course, however, the patterns of positions may be implemented in the context of any desired environment. Further, the aforementioned definitions may equally apply to the description below.

As shown in FIG. 13A, the substantially circumferential pattern is formed proximal to the inner circumference of the iris. In some embodiments, the predetermined pattern is a substantially circumferential pattern. The plurality of positions comprises N positions (e.g., positions 1302-*a*, 1302-*b*, 1302-*c*, 1302-*d* and the like where N=16 as shown in FIG. 13A), each of the N positions occurring at a first predetermined distance (e.g., distance d1 as shown in FIG. 13A) along a radius of the iris measured from the inner circumference of the iris. The N positions together form the substantially circumferential pattern which is substantially concentric with and proximal to the inner circumference of the iris (e.g., proximal to the iris limbus; external and adjacent to the sphincter muscle, for example targeting the iris stromal tissue and/or the iris dilator muscles). Additionally, laser patterns could be treated in multiple rows. For example, laser spots could be applied proximal to the iris root around the eye, and a second row could be applied inside (proximal) to the first row of spots. Such treatment may occur at the same treatment session or at a subsequent treatment session.

The N positions include a first position (e.g., position 1302-*a*) and a second position (e.g., position 1302-*b*) adjacent to the first position, wherein a center of the first position is separated from a center of the second position by a predetermined separation (e.g., separation x1 as shown in FIG. 12A) along the circumferential pattern. In some embodiments, each position of the plurality of positions corresponds to a treatment zone (e.g., a cut) on the patient's iris using the laser light beam. It will be appreciated that a certain amount of variation in the distance of each of the positions from the iris as measured from the center of the pupil may be incurred when using the predetermined patterns and that such variations are within the scope of the present disclosure. In some instances, such variation is intentional, in some instances such variation is due to imperfections in the symmetry of features of the subject eye, and in some instances such variation arises due to the precision or accuracy of the apparatus applying cuts to the eye. In some instance, such variation arises to any combination of the above-identified factors or for other reasons.

In some embodiments, the first predetermined distance has a value between 0.75 millimeters and 1.5 millimeters, the predetermined separation has a value between 50 micrometers and 300 micrometers, an average length of the first position (e.g., length 11 of position 1302-$c$) has a value between 25 micrometers and 200 micrometers, and N is a positive integer of value between 4 and 20. In some embodiments, the laser light beam is focused on the plurality of positions, thereby causing weakening of dilator muscle and scarification of posterior stroma.

Further, in some embodiments, a wavelength of the laser light beam has a value between 500 nanometers and 1100 nanometers. In some embodiments, a wavelength of the laser light beam has a value between 532 nanometers and 1064 nanometers. Additionally, the laser light source may be a pulse laser and an average duration of laser pulses has a value between 0.1 milliseconds and 20 milliseconds. In some embodiments, an average duration of laser pulses has a value between 0.5 milliseconds and 2 milliseconds.

In some embodiments, the laser light source is a pulse laser and an average repetition rate (e.g., frequency of repetition or pulsing) of laser pulses has a value between 0.5 Hertz and 800 Hertz. In some embodiments, an average repetition rate (e.g., frequency of repetition or pulsing) of laser pulses has a value between 20 Hertz and 60 Hertz.

In some embodiments, the laser light source is a pulse laser and the laser peak power has a value between 5 milliWatts and 1000 milliWatts. In some embodiments, the laser peak power has value of between 100 milliWatts and 300 milliWatts.

In some embodiments, the laser light source is a pulse laser with an average laser pulse energy having a value between 5 microJoules and 7500 microJoules. In some embodiments, the average laser pulse energy has a value between 200 microJoules and 1000 microJoules.

In some embodiments, an average laser power has a value between 1 milliWatt and 500 milliWatts. In some embodiments, the average laser power is between 10 milliWatts and 50 milliWatts.

Additional examples of laser parameters and operating conditions and ranges, that are used in some embodiments of the present disclosure are as follows: Number of laser-machined features between 100 and 25,000, (e.g., between 1000-5000); Diameter of posterior iris individual laser feature between 30 micrometers and 300 micrometers (e.g., diameter between 25 micrometers and 100 micrometers); Feature thickness between 50 micrometers and 200 micrometers e.g., between 75 micrometers and 125 micrometers); Fraction of iris area treated between 1% and 20% (e.g., about 5%); Clinical laser exposure time between 20 seconds and 100 seconds (e.g., between 30-60 seconds); and/or Focusing condition (e.g., spot size) between 0.3 and 0.6 NA (e.g., between 0.4-0.5 NA).

As shown in FIG. 13B, the substantially circumferential pattern is formed proximal to the outer circumference of the iris. In some embodiments, the predetermined pattern is a substantially circumferential pattern. The plurality of positions comprises N positions (e.g., positions 1304-$a$, 1304-$b$, 1304-$c$, 1304-$d$ and the like where N=16 as shown in FIG. 13B), each of the N positions occurring at a second predetermined distance (e.g., distance d2 as shown in FIG. 13B) along a radius of the iris measured from the outer circumference of the iris. The N positions together form the substantially circumferential pattern which is substantially concentric with and proximal to the outer circumference of the iris (e.g., the iris root). The N positions include a first position (e.g., position 1304-$a$) and a second position (e.g., position 1304-$b$) adjacent to the first position, wherein a center of the first position is separated from a center of the second position by a predetermined separation (e.g., separation x2 as shown in FIG. 13B) along the circumferential pattern. In some embodiments, each position of the plurality of positions corresponds to a treatment zone (e.g., a cut) on the patient's iris using the laser light beam.

In some embodiments, the second predetermined distance has a value between 0 and 1.5 millimeters, the predetermined separation has a value between 50 micrometers and 1 millimeter, an average length of the first position (e.g., length 12 of position 1304-$c$) has a value between 25 micrometers and 500 micrometers, and N is a positive integer of value between 4 and 20. In some embodiments, the laser light beam is focused on the plurality of positions, thereby causing weakening of dilator muscle and scarification of posterior stroma. Additionally, multiple spots may be placed at the same location and/or in an overlapping fashion at the same treatment session or at some later laser treatment session.

In some embodiments, for the predetermined pattern described with reference to FIG. 13B, a wavelength of the laser light beam has a value between 770 nanometers and 1700 nanometers. In some embodiments, a wavelength of the laser light beam has a value between 1000 nanometers and 1350 nanometers.

In some embodiments, the laser light beam is used for a first portion of the N positions of the predetermined pattern during a first session, and for a second portion of the N positions of the predetermined pattern during a second session at a time after the first session, where the time between the first session and the second session is more than five minutes, more than one hour more than one day, or more than one week.

In some embodiments, the laser light beam is used for each of the N positions of the predetermined pattern during a first session, and for all or a portion of the N positions of the predetermined pattern during a second session at a time after the first session, where the time between the first session and the second session may be micro seconds, seconds, minutes, hours, days, months, and/or years.

In some embodiments, the laser light beam is used for a portion of the N positions of the predetermined pattern during a first session, and for all or a portion of the N positions of the predetermined pattern during a second session at a time after the first session, where the time between the first session and the second session is more than five minutes, more than one hour more than one day, or more than one week.

In some embodiments, for any predetermined pattern disclosed herein, the laser light source is a pulse laser and an average duration of laser pulses has a value between 100 femtoseconds and 1000 femtoseconds. In some embodiments, an average duration of laser pulses has a value between 150 femtoseconds and 600 femtoseconds. Additionally, the laser light source may be a pulse laser and an average repetition rate (e.g., frequency of repetition or pulsing) of laser pulses has a value between 1 kiloHertz and 100 kiloHertzs. In some embodiments, an average repetition rate (e.g., frequency of repetition or pulsing) of laser pulses has a value between 10 kiloHertzs and 25 kiloHertzs.

In some embodiments, the laser light source is a pulse laser and an average laser peak power has a value between 1 Watts and 100 Watts. In some embodiments, the average laser peak power has value of 100 Ws. Additionally, the laser light source is a pulse laser and an average laser pulse energy has a value between 5 microJoules and 100 microJoules. In some embodiments, an average laser pulse energy has a value between 10 microJoules and 50 microJoules.

In some embodiments, an average laser power has a value between 100 milliWatts and 5000 milliWatts. In some embodiments, an average laser power has a value of 1000 MilliWatts Still yet, an average number of laser shots delivered on the patient's iris lies between 100,000 to 20 million. In some embodiments, an average number of laser shots delivered on the patient's iris is between 100,000 to 2 million.

Additional examples of laser parameters and operating conditions and ranges are as follows: Number of laser machined posterior features (offset features which may allow the laser to fire at a location different than where the aiming beam is focused) 50-300, (e.g., in some embodiments, a number of laser-machined posterior features is 100); Size of posterior iris laser-machined individual feature 50-200 micrometers diameter features (e.g., 100 micrometers in diameter); Depth of iris tissue treated: 50-200 micrometer deep features (e.g., 100 micrometer deep features); Fraction of iris area treated: 1-20%; Clinical laser exposure time: 30-120 seconds (e.g., 60 seconds); Focusing condition (e.g., spot size) 0.3-0.6 NA (e.g., 0.4-0.5 NA); and/or Separation of consecutive laser shots in scanning pattern: 1-10 micrometer, preferably 3-6 micrometer.

Figure 14A:
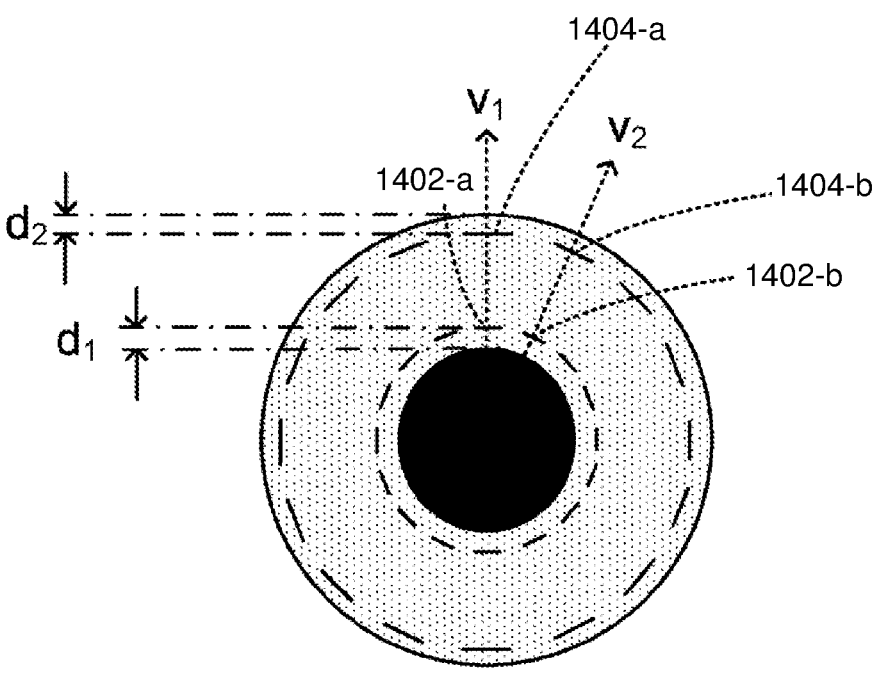
FIGS. 14A-14B illustrate substantially circumferential predetermined patterns (e.g., in dual concentric arrangements) of positions for delivering the laser light beam on one or more of the iris tissues of a patient's eye, in accordance with one embodiment.
Figure 14B:
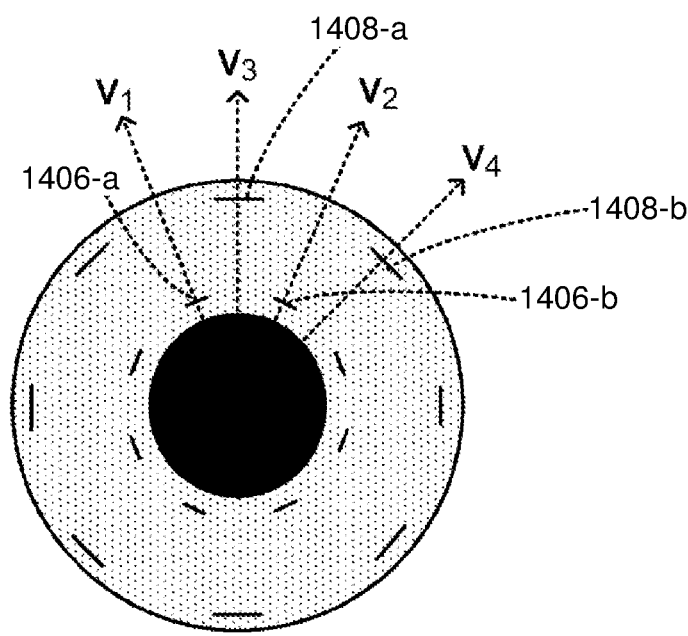

FIGS. 14A-14B illustrate substantially circumferential predetermined patterns (e.g., in dual concentric arrangements) of positions for delivering the laser light beam on one or more of the iris tissues of a patient's eye, in accordance with one embodiment. As an option, the substantially circumferential predetermined patterns may be implemented in the context of any one or more of the embodiments set forth in any previous and/or subsequent figure(s) and/or description thereof. Of course, however, the substantially circumferential predetermined patterns may be implemented in the context of any desired environment. Further, the aforementioned definitions may equally apply to the description below.

In some embodiments, the predetermined pattern is a substantially circumferential pattern. The plurality of positions comprises a (i) first set of M positions (e.g., positions 1402-*a*, 1402-*b* and the like where M=16, as shown in FIG. 14A; positions 1406-*a*, 1406-*b* and the like where M=8, as shown in FIG. 14B) and (ii) a second set of P positions (e.g., positions 1404-*a*, 1404-*b* and the like where P=16, as shown in FIG. 14A; positions 1408-*a*, 1408-*b* and the like where P=8, as shown in FIG. 14B).

Each position of the first set of M positions occurs at a first predetermined distance (e.g., distance $d_1$ as shown in FIG. 14A) along the radius of the iris measured from the inner circumference of the iris and the first set of M positions forms a first portion of the substantially circumferential pattern which is substantially concentric with and proximal to the inner circumference of the iris (e.g., proximal to the iris limbus; external and adjacent to the sphincter muscle, for example targeting the iris stromal tissue and/or the iris dilator muscles).

Each position of the second set of P positions occurs at a second predetermined distance (e.g., distance $d_2$ as shown in FIG. 14A) along the radius of the iris measured from the outer circumference of the iris and the first set of P positions forming a second portion of the substantially circumferential pattern which is substantially concentric with and proximal to the outer circumference of the iris (e.g., proximal to the iris root). In some embodiments, each position of the plurality of positions corresponds to a treatment zone (e.g., a cut) on the patient's iris using the laser light beam.

In some embodiments, the first predetermined distance has a value between 0.75 millimeters and 1.5 millimeters, the second predetermined distance has a value between 0 and 1.5 millimeters, and M and P are positive integers of values between 4 and 20.

FIG. 14A illustrates a substantially circumferential predetermined pattern of positions (e.g., in a dual concentric arrangement, with the positions placed in both concentric arrangements along the same radial vectors) for delivering the laser light beam on one or more of the iris tissues of a patient's eye, in accordance with some embodiments of the present disclosure.

In some embodiments, the first set of M positions includes (i) a first position (e.g., position 1402-*a*) with a center located along a first radial vector (vector v1, FIG. 14A) measured from the center of the pupil toward the outer circumference of the iris and (ii) a second position (e.g., position 1402-*b*), adjacent to the first position among the first set of M positions, located along a second radial vector (vector v2, FIG. 14A) measured from the center of the pupil toward the outer circumference of the iris. The second set of P positions includes a third position (e.g., position 1404-*a*) along the first radial vector (vector v1, FIG. 14A) and a fourth position (e.g., position 1404-*b*) adjacent to the third position along the second radial vector (vector v2, FIG. 14A).

Further, FIG. 14B may illustrate a substantially circumferential predetermined pattern of positions (e.g., in a dual concentric arrangement, with the positions placed in the two concentric arrangements along interleaved radial vectors) for delivering the laser light beam on one or more of the iris tissues of a patient's eye, in accordance with some embodiments of the present disclosure.

In some embodiments, the first set of M positions includes (i) a first position (e.g., position 1406-*a*) with a center located along a first radial vector (vector v1, FIG. 14B) measured from the center of the pupil toward the outer circumference of the iris and (ii) a second position (e.g., position 1406-*b*), adjacent to the first position among the first set of M positions, located along a second radial vector (vector v2, FIG. 14B) measured from the center of the pupil toward the outer circumference of the iris. The second set of P positions includes (i) a third position (e.g., position 1408-*a*) along a third radial vector (vector v3, FIG. 14B) and (ii) a fourth position (e.g., position 1408-*b*) adjacent to the third position along the fourth radial vector (vector v4, FIG. 14B). The third radial vector is located between the first radial vector and the second radial vector (e.g., v3 is located between v1 and v2, FIG. 14B); and the second radial vector is located between the third radial vector and the fourth radial vector (e.g., v2 is located between v3 and v4, FIG. 14B).

Figure 15:
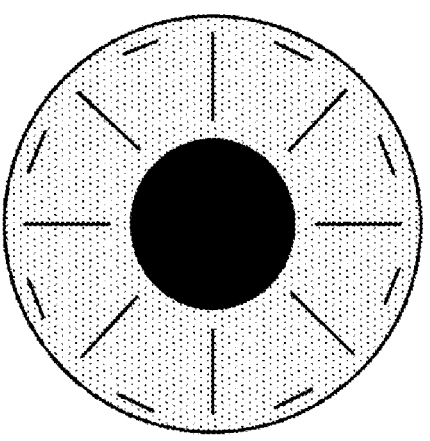
FIG. 15 illustrates a combination of substantially radial and substantially circumferential patterns of positions for delivering the laser light beam on one or more of the iris tissues of a patient's eye, in accordance with one embodiment.

FIG. 15 illustrates a combination of substantially radial and substantially circumferential patterns of positions for delivering the laser light beam on one or more of the iris tissues of a patient's eye, in accordance with one embodiment. As an option, the patterns of positions may be implemented in the context of any one or more of the embodiments set forth in any previous and/or subsequent figure(s) and/or description thereof. Of course, however, the patterns of positions may be implemented in the context of any desired environment. Further, the aforementioned definitions may equally apply to the description below.

In one embodiment, FIG. 15 illustrates a combination of substantially radial (e.g., as explained with reference to FIGS. 12A-12B) and substantially circumferential patterns (e.g., as explained with reference to FIGS. 13A-13B) of positions for delivering the laser light beam on one or more of the iris tissues of a patient's eye, in accordance with some embodiments of the present disclosure.

Figure 16:
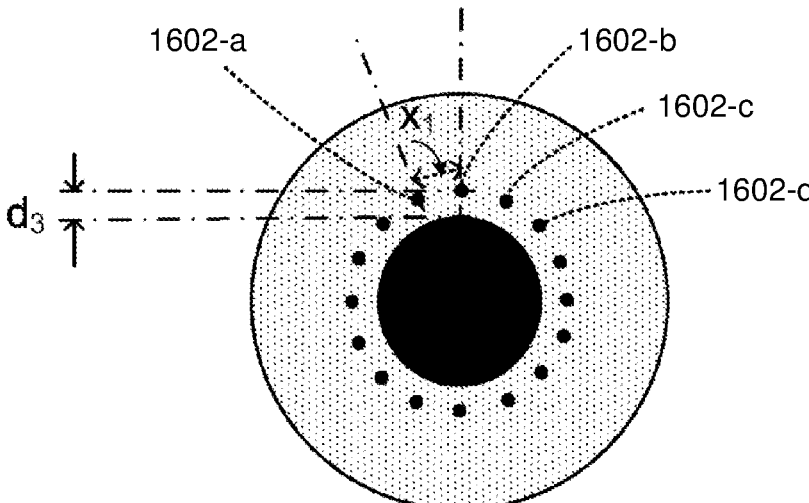
FIG. 16 illustrates a substantially circular predetermined spot pattern of positions for delivering the laser light beam on one or more of the iris tissues of a patient's eye, in accordance with one embodiment.

FIG. 16 illustrates a substantially circular predetermined spot pattern of positions for delivering the laser light beam on one or more of the iris tissues of a patient's eye, in accordance with one embodiment. As an option, the pattern of positions may be implemented in the context of any one or more of the embodiments set forth in any previous and/or subsequent figure(s) and/or description thereof. Of course, however, the pattern of positions may be implemented in the context of any desired environment. Further, the aforementioned definitions may equally apply to the description below.

In some embodiments, the predetermined pattern is a substantially circular spot pattern. The plurality of positions comprises N positions (e.g., positions 1602-a, 1602-b, 1602-c, 1602-d and the like where N=16 as shown in FIG. 16), each of the N positions occurring at a third predetermined distance (e.g., distance d3 as shown in FIG. 16) along a radius of the iris measured. from the inner circumference of the iris. The N positions together form the substantially circular spot pattern which is substantially concentric with and proximal to the inner circumference of the iris (e.g., proximal to the iris limbus; external and adjacent to the sphincter muscle, for example targeting the iris stromal tissue and/or the iris dilator muscles). The N positions include a first spot position (e.g., position 1602-a) and a second spot position (e.g., position 1602-b) adjacent to the first spot position, wherein a center of the first spot position is separated from a center of the second spot position by a predetermined separation (e.g., separation x1 as shown in FIG. 16) along the circumferential pattern. In some embodiments, each position of the plurality of positions corresponds to a treatment zone (e.g., a cut) on the patient's iris using the laser light beam.

In some embodiments, the third predetermined distance has a value between 0.75 millimeters and 1.5 millimeters, the predetermined separation has a value between 0 micrometers and 300 micrometers, an average diameter of the first spot position has a value between 10 micrometers to 300 micrometers, and N is a positive integer of value between 4 and 20. In some embodiments, the laser light beam is focused on the plurality of positions, thereby cousin contraction of collagen in stroma and weakening of dilator muscle on the posterior iris.

In some embodiments, for the predetermined pattern described with reference to FIG. 16, a wavelength of the laser light beam has a value between 532 nanometers and 1100 nanometers. In some embodiments, a wavelength of the laser light beam has a value between 900 nanometers and 1064 nanometers.

In some embodiments, for the predetermined pattern described with reference to FIG. 16, the laser light source is a pulse laser and an average duration of laser pulses has a value between 10 milliseconds and 100 milliseconds. In some embodiments, an average duration of laser pulses has a value between 40 milliseconds and 60 milliseconds.

In some embodiments, for the predetermined pattern described with reference to FIG. 16, the laser light source is a pulse laser and an average repetition rate (e.g., frequency of repetition or pulsing) of laser pulses has a value between 2 Hertz and 40 Hertz. In some embodiments, an average repetition rate (e.g., frequency of repetition or pulsing) of laser pulses has a value between 5 Hertz and 15 Hertz.

In some embodiments, for the predetermined pattern described with reference to FIG. 16, the laser light source is a pulse laser and a laser peak power has a value between 0.5 Watt and 6 Watts. In some embodiments, the laser peak power has value of between 4 Watts and 6 Watts.

In some embodiments, for the predetermined pattern described with reference to FIG. 16, the laser light source is a pulse laser and an average laser pulse energy has a value between 5 milliJoules and 250 milliJoules. In some embodiments, an average laser pulse energy has a value between 80 milliJoules and 120 milliJoules.

In some embodiments, for the predetermined pattern described with reference to FIG. 16, an average laser power has a value between 0.2 Watt and 1 Watt. In some embodiments, an average laser power has a value between 0.4 Watt to 0.6 Watt. Additionally, for the predetermined pattern described with reference to FIG. 16, an average number of laser shots delivered on the patient's iris lies between 100 and 1000. In some embodiments, an average number of laser shots delivered on the patient's iris is between 200 and 300.

Additional examples of laser parameters and operating conditions and ranges are as described as follows: Fraction of Iris to be treated: 1%-20% (e.g., 5-10%); Total Clinical treatment time: 15-120 seconds (e.g., 40-60 seconds); Target Increase in Tissue Temperature: 10-60 degrees Celsius (e.g., target increase 35-45 degrees Celsius); and/or Spot Size of Treatment Zone: 40-350 micrometers (e.g., 150-260 micrometers).

Figure 17:
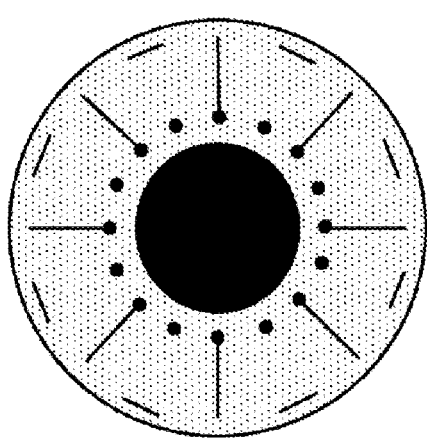
FIG. 17 illustrates a combination of substantially radial, substantially circumferential, and substantially circular spot patterns of positions for delivering the laser light beam on one or more of the iris tissues of a patient's eye, in accordance with one embodiment.

FIG. 17 illustrates a combination of substantially radial, substantially circumferential, and substantially circular spot patterns of positions for delivering the laser light beam on one or more of the iris tissues of a patient's eye, in accordance with one embodiment. As an option, the patterns of positions may be implemented in the context of any one or more of the embodiments set forth in any previous and/or subsequent figure(s) and/or description thereof. Of course, however, the patterns of positions may be implemented in the context of any desired environment. Further, the aforementioned definitions may equally apply to the description below.

Additionally, FIG. 17 illustrates a combination of substantially radial (e.g., as explained with reference to FIGS. 12A-12B), substantially circumferential (e.g., as explained with reference to FIGS. 13A-13B), and substantially circular spot patterns (e.g., as explained with reference to FIG. 16) of positions for delivering the laser light beam on one or more of the iris tissues of a patient's eye, in accordance with some embodiments of the present disclosure.

FIG. 18 illustrates a method 1800 for creating a treatment pattern based on a color map of the eye, in accordance with one embodiment. As an option, the method 1800 may be implemented in the context of any one or more of the embodiments set forth in any previous and/or subsequent figure(s) and/or description thereof. Of course, however, the method 1800 may be implemented in the context of any desired environment. Further, the aforementioned definitions may equally apply to the description below.

As shown, method 1800 comprises determining a color map of the patient's eye. See operation 1802. Additionally, a treatment pattern may be created based on the color map of the eye. See operation 1804. A laser illuminate beam may be aligned based on the treatment pattern. See operation 1806. In addition, the laser may be delivered based on the treatment pattern 1804. See operation 1808.

As discussed herein, the color map (consistent with FIGS. 7-8) may be used to retrieve a set of preconfigured instructions (on laser treatment) for a particular eye color. Additionally, the color map may be used for purposes of changing a current color of the eye to a desired color.

Figure 19:
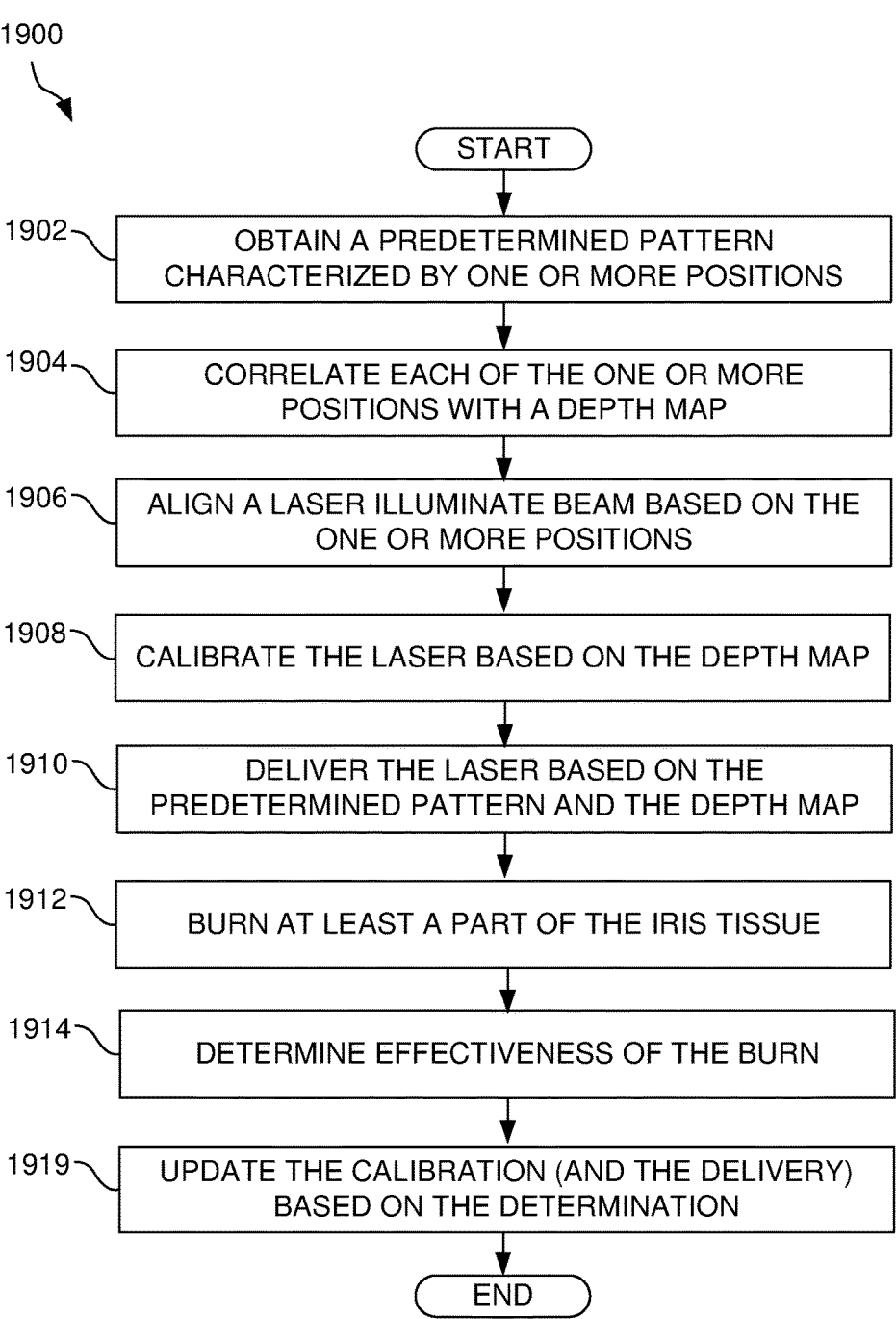
FIG. 19 illustrates a method for updating a calibration of the laser based on an effectiveness of burning, in accordance with one embodiment.

FIG. 19 illustrates a method 1900 for updating a calibration of the laser based on an effectiveness of burning, in accordance with one embodiment. As an option, the method 1900 may be implemented in the context of any one or more of the embodiments set forth in any previous and/or subsequent figure(s) and/or description thereof. Of course, however, the method 1900 may be implemented in the context of any desired environment. Further, the aforementioned definitions may equally apply to the description below.

As shown, method 1900 comprises obtaining a predetermined pattern characterized by one or more positions. See operation 1902. Each of the one or more positions may be correlated with a spot treatment point. Additionally, each of the one or more positions may be correlated with a depth map 330. See operation 1904. Such depth map may be obtained via an initial scan of the eye (consistent with operation 102). Additionally, any type of eye map (color map, depth map, position map, etc.) may be used for purposes of correlating with the one or more positions. Further, a laser illuminate beam may be aligned based on the one or more positions. See operation 1906. Such alignment may include one of general positioning (x and y coordinate) as well as depth positioning (z coordinate). Further, the laser illuminate beam may be composed of more than one laser beam, where each laser beam may be used for a different purpose (e.g. treatment, focusing, aiming, guiding, etc.).

In addition, the laser may be calibrated based on the depth map 330. See operation 1908. Still yet, the laser may be delivered based on the predetermined pattern and the depth map. See operation 1910. Such delivery may be consistent with the modulated treatment.

Additionally, at least a part of the iris tissue may be burned. See operation 1912. It is to be understood that burning, as used within the context of the present description, may encompass any or all of altering the tissue, heating, cutting, weakening, and/or creating a scar.

Further, the effectiveness of the burning is determined. See operation 1914. Should the burning be determined to not be effective, the calibration (and the delivery) may be updated accordingly. See operation 1919. In this manner, the modulated treatment may be personalized for the individual patient and the individual eye, and may be further modulated based on information obtained in the course of treatment.

In various embodiments, the method 1900 (and/or any of the methods disclosed herein) may be governed by instructions that are stored in a computer readable storage medium and that are executed by one or more processors of one or more servers. Each of the operations shown in the method 1900 may correspond to instructions stored in a computer memory or computer readable storage medium. The computer readable storage medium may include a magnetic or optical disk storage device, solid state storage devices such as flash memory, or other non-volatile memory device or devices. The computer readable instructions stored on the computer readable storage medium are in source code, assembly language code, object code, or other instruction format that is interpreted by one or more processors.

Additionally, the laser system may obtain (e.g., retrieves and/or generates) a predetermined pattern characterized by a plurality of positions along a plurality of spatially distributed iris tissues of an eye of a patient. For example, the laser system may obtain a substantially radial pattern, a substantially circumferential pattern, a combination of substantially radial and substantially circumferential patterns, a substantially circular spot pattern, a combination of substantially radial, substantially circumferential, or substantially circular spot patterns. The predetermined patterns may be characterized by a corresponding plurality of positions along a plurality of spatially distributed iris tissues (e.g., the iris limbus tissue, the iris stromal tissue, and/or the iris dilator muscle tissue).

The laser system may align a laser illumination light beam in accordance with one or more of the plurality of positions along a plurality of spatially distributed iris tissues. In some embodiments, the laser system may obtain one or more laser parameters (e.g., wavelength of laser light, average duration of laser pulses, average pulse repetition rate of laser pulses, time of treatment or delivery of laser pulses, and the like) in accordance with the obtained predetermined pattern. In other words, in some embodiments, one or more of the laser parameters are selected in accordance with the predetermined pattern; different sets of laser parameters are selected for different corresponding predetermined patterns. If a combination of predetermined patterns is used (e.g., a combination of substantially radial and substantially circumferential patterns; or a combination of radial, substantially circumferential, and substantially circular spot patterns), then a corresponding combination of laser parameters may be used in accordance with the selected combination of predetermined patterns.

The laser system may deliver the laser illumination light beam in the predetermined pattern on a surface of the eye of the patient. Additionally, the laser system may burn (e.g., heat to a predefined temperature and/or treats) at least a subset of the spatially distributed iris tissues, by the delivery of the laser illumination light beam in the predetermined pattern (e.g., causing the subset of iris tissues to heat, contract, be cut, or scarify), thereby resulting in a decrease in diameter of the pupil of the eye.

FIG. 20 illustrates an exemplary pattern 2000, in accordance with one embodiment. As an option, the exemplary pattern 2000 may be implemented in the context of any one or more of the embodiments set forth in any previous and/or subsequent figure(s) and/or description thereof. Of course, however, the exemplary pattern 2000 may be implemented in the context of any desired environment. Further, the aforementioned definitions may equally apply to the description below.

As shown, the exemplary pattern 2000 includes an eye 2002, an iris 2004, a pupil 2006, and a peripheral pattern configuration 2008. In one embodiment, the peripheral pattern configuration 2008 may include one hundred dots. Of course, it is to be appreciated that any number of dots may exist for the peripheral pattern configuration 2008 as needed. In one embodiment, each spot of the peripheral pattern configuration 2008 may be 100 microns in diameter. Of course, the sizing may be preconfigured and set as desired.

Additionally, as shown in the peripheral pattern configuration 2008, the treatment spots may be located along the lateral exterior of the iris (such as near the iris root).

Additionally, the treatment spots may be configured such that the depth of the treatment reaches the dilator muscle of the iris.

Figure 21:
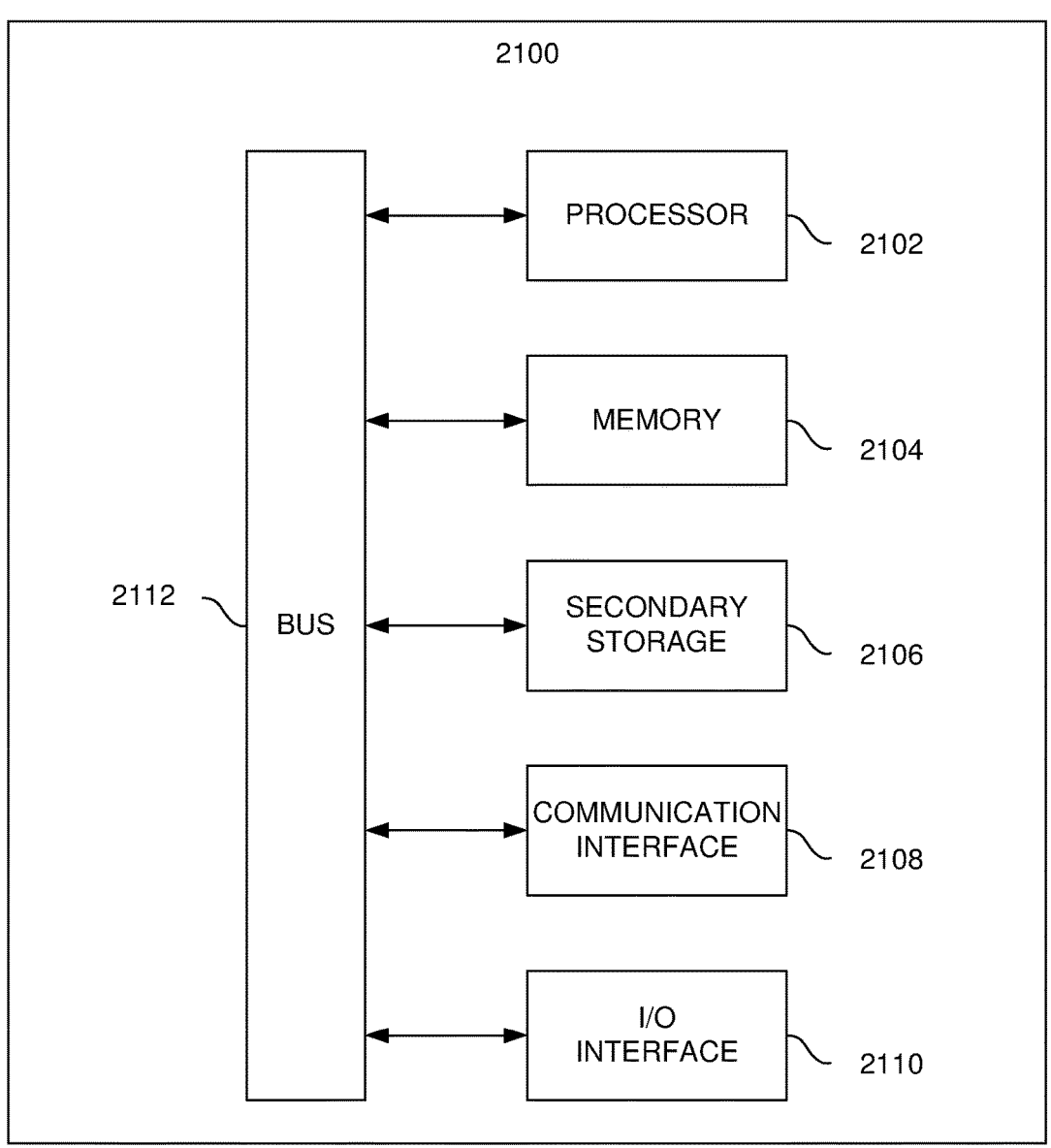
FIG. 21 illustrates an exemplary system, in accordance with one embodiment.

FIG. 21 illustrates an exemplary system 2100, in accordance with one embodiment. As an option, the system 2100 may be implemented in the context of any devices of a network architecture, or in any desired environment.

As shown, a system 2100 is provided including at least one central processor 2102 which is connected to a communication bus 2112. The system 2100 also includes main memory 2104 [e.g., random access memory (RAM), etc.]. The system 2100 also includes a graphics processor 2108 and a display 2110.

The system 2100 may also include a secondary storage 2106. The secondary storage 2106 includes, for example, a hard disk drive and/or a removable storage drive, representing a floppy disk drive, a magnetic tape drive, a compact disk drive, etc. The removable storage drive reads from and/or writes to a removable storage unit in a well known manner.

Computer programs, or computer control logic algorithms, may be stored in the main memory 2104, the secondary storage 2106, and/or any other memory, for that matter. Such computer programs, when executed, enable the system 2100 to perform various functions (as set forth above, for example). Memory 2104, storage 2106 and/or any other storage are possible examples of non-transitory computer-readable media. It is noted that the techniques described herein, in an aspect, are embodied in executable instructions stored in a computer readable medium for use by or in connection with an instruction execution machine, apparatus, or device, such as a computer-based or processor-containing machine, apparatus, or device. It will be appreciated by those skilled in the art that for some embodiments, other types of computer readable media are included which may store data that is accessible by a computer, such as magnetic cassettes, flash memory cards, digital video disks, Bernoulli cartridges, random access memory (RAM), read-only memory (ROM), and the like.

As used here, a "computer-readable medium" includes one or more of any suitable media for storing the executable instructions of a computer program such that the instruction execution machine, system, apparatus, or device may read (or fetch) the instructions from the computer readable medium and execute the instructions for carrying out the described methods. Suitable storage formats include one or more of an electronic, magnetic, optical, and electromagnetic format. A non-exhaustive list of conventional exemplary computer readable medium includes: a portable computer diskette; a RAM; a ROM; an erasable programmable read only memory (EPROM or flash memory); optical storage devices, including a portable compact disc (CD), a portable digital video disc (DVD), a high definition DVD (HD-DVD™), a BLU-RAY disc; and the like.

It should be understood that the arrangement of components illustrated in the Figures described are exemplary and that other arrangements are possible. It should also be understood that the various system components (and means) defined by the claims, described below, and illustrated in the various block diagrams represent logical components in some systems configured according to the subject matter disclosed herein.

For example, one or more of these system components (and means) may be realized, in whole or in part, by at least some of the components illustrated in the arrangements illustrated in the described Figures. In addition, while at least one of these components are implemented at least partially as an electronic hardware component, and therefore constitutes a machine, the other components may be implemented in software that when included in an execution environment constitutes a machine, hardware, or a combination of software and hardware.

More particularly, at least one component defined by the claims is implemented at least partially as an electronic hardware component, such as an instruction execution machine (e.g., a processor-based or processor-containing machine) and/or as specialized circuits or circuitry (e.g., discreet logic gates interconnected to perform a specialized function). Other components may be implemented in software, hardware, or a combination of software and hardware. Moreover, some or all of these other components may be combined, some may be omitted altogether, and additional components may be added while still achieving the functionality described herein. Thus, the subject matter described herein may be embodied in many different variations, and all such variations are contemplated to be within the scope of what is claimed.

In the description above, the subject matter is described with reference to acts and symbolic representations of operations that are performed by one or more devices, unless indicated otherwise. As such, it will be understood that such acts and operations, which are at times referred to as being computer-executed, include the manipulation by the processor of data in a structured form. This manipulation transforms the data or maintains it at locations in the memory system of the computer, which reconfigures or otherwise alters the operation of the device in a manner well understood by those skilled in the art. The data is maintained at physical locations of the memory as data structures that have particular properties defined by the format of the data. However, while the subject matter is being described in the foregoing context, it is not meant to be limiting as those of skill in the art will appreciate that various of the acts and operations described hereinafter may also be implemented in hardware.

To facilitate an understanding of the subject matter described herein, many aspects are described in terms of sequences of actions. At least one of these aspects defined by the claims is performed by an electronic hardware component. For example, it will be recognized that the various actions may be performed by specialized circuits or circuitry, by program instructions being executed by one or more processors, or by a combination of both. The description herein of any sequence of actions is not intended to imply that the specific order described for performing that sequence must be followed. All methods described herein may be performed in any suitable order unless otherwise indicated herein or otherwise clearly contradicted by context.

The use of the terms "a" and "an" and "the" and similar referents in the context of describing the subject matter (particularly in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Furthermore, the foregoing description is for the purpose of illustration only, and not for the purpose of limitation, as the scope of protection sought is defined by the claims as set forth hereinafter together with any equivalents thereof entitled to. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

The embodiments described herein included the one or more modes known to the inventor for carrying out the claimed subject matter. Of course, variations of those embodiments will become apparent to those of ordinary skill in the art upon reading the foregoing description. The inventor expects skilled artisans to employ such variations as appropriate, and the inventor intends for the claimed subject matter to be practiced otherwise than as specifically described herein. Accordingly, this claimed subject matter includes all modifications and equivalents of the subject matter recited in the claims appended hereto as permitted by applicable law. Moreover, any combination of the above-described elements in all possible variations thereof is encompassed unless otherwise indicated herein or otherwise clearly contradicted by context.

What is claimed is:

1. A laser system, comprising:

a laser which includes radiation which is focusable as a laser illumination light beam;

a non-transitory memory storing instructions; and one or more processors in communication with the non-transitory memory, wherein the one or more processors execute the instructions to:

scan an eye of a patient to produce a scan result, wherein the scan result comprises at least one of optical coherence tomography (OCT), thermal imaging, or ultrasound data specifically of iris dilator muscle tissue depth and density;

create a mapping of the eye based on the scan result, wherein the mapping includes at least one of a depth map, optical density map, or color map, and wherein the mapping includes a three-dimensional depth map of iris dilator muscle tissue location;

create a modulated treatment of the eye based on the mapping, wherein the modulated treatment is configured to cause a decrease in diameter of a pupil of the eye by targeting at least a subset of iris dilator muscle tissue;

deliver the laser illumination light beam to a first location on the eye of the patient in accordance with the modulated treatment; and determine an effectiveness of the modulated treatment at the first location in real-time during delivery of the last illumination light beam based on at least one of thermal imaging, optical coherence tomography (OCT), or ultrasound;

wherein determining the effectiveness comprises measuring at least one of thermal uptake, depth and density, or change in optical density specifically of the iris dilator muscle tissue;

wherein determining the effectiveness comprises comparing measurements at the first location against the three-dimensional depth map to verify sufficient laser penetration to the iris dilator muscle tissue; wherein the modulated treatment is automatically updated based on the determined effectiveness at the first location, and wherein the updated modulated treatment is used to guide treatment parameters for one or more second locations on the eye; and wherein the modulated treatment is updated by adjusting at least one of laser power, pulse duration, or focal depth based on whether the measured effectiveness indicates sufficient weakening of the iris dilator muscle's ability to dilate the pupil and based on the comparison of the measurements against the three-dimensional depth map.

2. The laser system of claim 1, wherein the one or more processors further execute the instructions to:

receive feedback for the modulated treatment based on the delivering of the laser illumination light beam to the first location on the eye, using the laser scanning system, wherein:

when the feedback aligns with expected results of the modulated treatment, deliver the laser illumination light beam to one or more second locations on the eye of the patient in accordance with the modulated treatment; or when the feedback conflicts with the expected results of the modulated treatment, update the modulated treatment based on the feedback, and deliver the laser illumination light beam to the one or more second locations on the eye of the patient in accordance with the updated modulated treatment.

3. The laser system of claim 2, wherein the laser system is configured such that the feedback includes a muscle response of the eye.

4. The laser system of claim 1, wherein the one or more processors further execute the instructions to:

while delivering the laser illumination light beam to the first location on the eye or to the one or more second locations on the eye, track the eye; and guide the laser illumination light beam based on the tracking.

5. The laser system of claim 1, wherein the one or more processors further execute the instructions to:

burn, using the laser illumination light beam, the at least a subset of iris dilator muscle tissue of the eye or at least subset of iris sphincter muscle tissue of the eye, wherein the burning causes a decrease in diameter of a pupil of the eye.

6. The laser system of claim 1, wherein the laser system is configured such that the modulated treatment includes at least two of:

a predetermined pattern, a predetermined depth, or a color, wherein the color is associated with at least one of: an effective pulse of the laser illumination light beam, an effective depth for the laser illumination light beam, a power, or a duration of pulse associated with laser illumination light beam.

7. The laser system of claim 1, wherein the laser system is configured such that the laser is a pulse laser and the laser illumination light beam comprises a sequence of a plurality of light pulses with an average repetition rate between two consecutive light pulses of the plurality of light pulses between 0.5 Hertz and 100 kiloHertz.

8. The laser system of claim 1, wherein the laser system is configured such that the laser illumination light beam comprises a sequence of light pulses of average time duration between 10 milliseconds and 100 milliseconds.

9. The laser system of claim 1, wherein the laser system is configured such that the laser illumination light beam comprises a sequence of light pulses of average time duration between 1 millisecond and 10 milliseconds.

10. The laser system of claim 1, wherein the laser system is configured such that the laser illumination light beam comprises a sequence of light pulses of average time duration between 100 femtoseconds and 1 millisecond.

11. The laser system of claim 1, wherein the one or more processors further execute the instructions to:

monitor iris muscle contraction in real-time during delivery of the laser illumination light beam, and adjust laser power or pulse duration based on observed changes in pupil diameter to optimize targeting of the iris dilator muscle tissue;

or create the modulated treatment to include a radial treatment pattern that follows anatomical pathways of the iris dilator muscle tissue, wherein the radial treatment pattern extends from an iris root toward a pupil margin to maximize weakening of the dilator muscle's ability to expand the pupil.

12. The laser system of claim 1, wherein the one or more processors further execute the instructions to receive feedback in the form of a muscle response of the iris sphincter muscle, and increase or decrease power or pulse duration of the laser based on whether a visible muscle response is observed.

13. The laser system of claim 1, wherein the laser system comprises a first laser beam for treatment and a second laser beam for aiming, wherein the second laser beam is focused on an anterior surface of the iris and the first laser beam converges at a distance of 50 to 250 microns deeper than the focus point of the second laser beam.

14. The laser system of claim 1, wherein the one or more processors further execute the instructions to perform modulated treatment on a spot-by-spot basis, wherein an active OCT is used to determine whether a last treatment spot was of appropriate depth and density to produce a desired treatment result.

15. The laser system of claim 1, wherein the one or more processors further execute the instructions to correlate each of one or more positions of the modulated treatment with a spot treatment point and correlate the one or more positions with a depth map obtained via an initial scan of the eye, and wherein the laser is calibrated based on the depth map and delivered based on a predetermined pattern and the depth map.

16. The laser system of claim 1, wherein the one or more processors further execute the instructions to determine whether the patient's eye has moved, and if the eye has moved, recalibrate the mapping by modifying offset laser points, laser beam angles, power of the laser beam, wattage of the laser beam, or depth of laser point.

17. The laser system of claim 1, wherein the laser system is configured to operate in a continuous wave format where a laser burn is initiated and a delivery site is moved to various locations without pulses in a continuous line, providing continuous delivery of the laser beam to the eye.

18. The laser system of claim 1, wherein the laser system is configured to apply laser spots in multiple rows, wherein laser spots are applied proximal to an iris root around the eye, and a second row is applied inside proximal to the first row of spots, wherein such treatment occurs at a same treatment session or at a subsequent treatment session.

19. The laser system of claim 1, wherein the one or more processors further execute the instructions to:

create the mapping by determining thickness variations of the iris tissue at multiple locations around the eye, wherein an eye-specific pattern is configured to compensate for the thickness variations by adjusting at least one of laser power, pulse duration, or focal depth at each location based on the determined thickness at that location, such that the laser treatment delivered to the iris dilator muscle tissue remains consistent at all locations notwithstanding the thickness variations.

20. The laser system of claim 1, wherein:

the scan result comprises optical coherence tomography (OCT) data that measures depth and optical density of iris tissue at a plurality of positions along spatially distributed iris tissues;

the three-dimensional depth map identifies locations of the iris dilator muscle tissue at the plurality of positions;

determining the effectiveness in real-time comprises using OCT to measure a change in optical density at the first location during delivery of the laser illumination light beam; and the modulated treatment is automatically updated for a second location by adjusting focal depth based on comparing the measured change at the first location against the three-dimensional depth map to determine whether the laser illumination light beam sufficiently penetrated to the iris dilator muscle tissue at the first location.

* * * * *